(12) United States Patent
McCoy et al.

(10) Patent No.: US 11,707,580 B2
(45) Date of Patent: Jul. 25, 2023

(54) THERMIC INFUSION SYSTEM DRY TUBE DETECTOR

(71) Applicant: Life Warmer Inc., Canton, CT (US)

(72) Inventors: James Kevin McCoy, Garland, TX (US); Jared A. Smothermon, Lucas, TX (US)

(73) Assignee: Life Warmer Inc., Canton, CT (US)

( * ) Notice: Subject to any disclaimer, the term of this patent is extended or adjusted under 35 U.S.C. 154(b) by 336 days.

(21) Appl. No.: 16/672,901

(22) Filed: Nov. 4, 2019

(65) Prior Publication Data
US 2020/0061308 A1   Feb. 27, 2020

Related U.S. Application Data

(63) Continuation-in-part of application No. 15/557,006, filed on Sep. 8, 2017, now Pat. No. 10,780,258.

(51) Int. Cl.
*A61M 5/44* (2006.01)
*A61M 39/08* (2006.01)
*A61M 5/14* (2006.01)

(52) U.S. Cl.
CPC ............ *A61M 5/44* (2013.01); *A61M 5/14* (2013.01); *A61M 39/08* (2013.01); *A61M 2205/36* (2013.01); *A61M 2205/3653* (2013.01)

(58) Field of Classification Search
CPC ........ A61M 1/369; A61M 5/14; A61M 5/142; A61M 5/44; A61M 2205/36; A61M 2205/3606; A61M 2205/3633; A61M 2205/3653; A61M 2205/3666; A61M 2205/3673
See application file for complete search history.

(56) References Cited

U.S. PATENT DOCUMENTS

| 1,995,302 A | 3/1935 | Harold |
| 2,063,902 A | 12/1936 | Beasley |
| 2,087,586 A | 7/1937 | Tishman |

(Continued)

FOREIGN PATENT DOCUMENTS

| DE | 102007056169 A1 | 5/2009 |
| DE | 10211004481 A1 | 2/2011 |

(Continued)

OTHER PUBLICATIONS

USPTO; First Office Action dated Feb. 20, 2019 in parent U.S. Appl. No. 15/557,006, filed Sep. 8, 2017.

(Continued)

*Primary Examiner* — Kami A Bosworth
(74) *Attorney, Agent, or Firm* — Robert H. Frantz

(57) ABSTRACT

A method for improved controlling of a thermic infusion system having a one tubal segment and a thermal element to heat an infusion fluid carried within the tubal segment, and having at least one sensor positioned within the thermic infusion system comprising regulating energy provided to the sensor for a first period of time to sense a self-heating effect of the at least one sensor due to a dry tube; responsive to detecting a dry tube, preventing energizing the thermal element; responsive to detecting a non-dry tube, regulating energy provided to the sensor for a second period of time to sense a temperature of an infusion fluid carried within the at least one tubal segment.

16 Claims, 13 Drawing Sheets

(56) References Cited

U.S. PATENT DOCUMENTS

| | | | |
|---|---|---|---|
| 2,102,523 A | 12/1937 | Ferrara | |
| 2,357,238 A | 8/1944 | Trimble | |
| 3,064,649 A | 11/1962 | Lee | |
| 3,140,716 A | 7/1964 | Harrison | |
| 3,275,802 A | 9/1966 | Vandivere | |
| 3,315,681 A | 4/1967 | Poppendiek | |
| 3,370,153 A | 2/1968 | Fresne | |
| 3,425,415 A | 2/1969 | Gordon | |
| 3,475,590 A | 10/1969 | Pins | |
| 3,485,245 A | 12/1969 | Lahr | |
| 3,518,393 A | 6/1970 | Besselling | |
| 3,551,641 A | 12/1970 | Fruhan | |
| 3,553,429 A | 1/1971 | Nelson | |
| 3,590,215 A | 6/1971 | Anderson | |
| 3,614,385 A | 10/1971 | Horstman | |
| 3,768,977 A | 10/1973 | Brumfield | |
| 3,908,652 A | 9/1975 | Weissenger | |
| 3,976,129 A | 8/1976 | Silver | |
| 4,038,519 A | 7/1977 | Foucras | |
| 4,167,663 A | 10/1979 | Granzow, Jr. et al. | |
| 4,177,816 A | 12/1979 | Torgeson | |
| 4,293,762 A | 10/1981 | Ogawa | |
| 4,309,592 A * | 1/1982 | Le Boeuf | A61M 1/369 165/46 |
| 4,314,143 A | 2/1982 | Bilstad | |
| 4,358,664 A | 11/1982 | Kronseder | |
| 4,532,414 A | 7/1985 | Shah | |
| 4,574,876 A | 3/1986 | Aid | |
| 4,623,333 A | 11/1986 | Fried | |
| 4,678,460 A | 7/1987 | Rosner | |
| 4,707,587 A | 11/1987 | Greenblatt | |
| 4,735,609 A | 4/1988 | Comeau | |
| 4,759,749 A | 7/1988 | Verkaart | |
| 4,782,212 A | 11/1988 | Bakke | |
| 4,801,777 A | 1/1989 | Auerbach | |
| 5,063,994 A | 11/1991 | Verkaart | |
| 5,097,898 A | 3/1992 | Verkaart | |
| 5,108,372 A | 4/1992 | Swenson | |
| 5,125,069 A | 6/1992 | O'Boyle | |
| 5,250,032 A | 10/1993 | Carter | |
| 5,254,090 A | 10/1993 | Lombardi | |
| 5,254,094 A | 10/1993 | Starkey | |
| 5,381,510 A | 1/1995 | Ford | |
| 5,875,282 A | 2/1999 | Jordan | |
| 6,142,974 A | 11/2000 | Kistner | |
| 6,641,556 B1 | 11/2003 | Shigezawa | |
| 7,158,719 B2 | 1/2007 | Cassidy | |
| 7,741,815 B2 | 6/2010 | Cassidy | |
| 8,150,244 B2 | 4/2012 | Cassidy | |
| 8,660,415 B2 | 2/2014 | Cassidy | |
| 8,690,842 B2 | 4/2014 | Lopez | |
| 2001/0011585 A1 | 8/2001 | Cassidy | |
| 2002/0120314 A1 | 8/2002 | Evans et al. | |
| 2003/0114795 A1 | 6/2003 | Faries, Jr. et al. | |
| 2006/0020255 A1 | 1/2006 | Cassidy et al. | |
| 2006/0150792 A1 | 7/2006 | Cazzini | |
| 2007/0142773 A1 | 6/2007 | Rosiello et al. | |
| 2008/0234619 A1 | 9/2008 | Fauset | |
| 2009/0319011 A1 | 12/2009 | Rosiello | |
| 2010/0025328 A1 | 2/2010 | Davies et al. | |
| 2010/0059498 A1 | 3/2010 | Hansen | |
| 2011/0098642 A1 | 4/2011 | Cassidy | |
| 2011/0202034 A1 | 8/2011 | Lopez | |
| 2014/0169775 A1 | 6/2014 | Cassidy | |
| 2014/0276587 A1 | 9/2014 | Imran | |
| 2017/0000973 A1 | 1/2017 | Otake et al. | |
| 2018/0064921 A1 | 3/2018 | Pettini | |

FOREIGN PATENT DOCUMENTS

| | | | |
|---|---|---|---|
| EP | 1462137 B1 | 12/2006 | |
| WO | 0002608 A1 | 1/2000 | |
| WO | 0107109 A1 | 2/2001 | |
| WO | 2011137266 A1 | 11/2011 | |
| WO | 2014118313 A1 | 7/2014 | |

OTHER PUBLICATIONS

European Patent Office; "Communication prusuant to Article 94(3) EPC"; dated May 12, 2020 in related PCT/EPO patent application No. 16 712 595.4-1122.

Patent Translate; "Description DE102011004481A1"; machine translated description from Item #1 Stihler Electronic GmbH listed in the Foreign Patent Documents section of this IDS.

Patent Translate; "Description DE102007056169A1"; machine translated description from Item #2 Volker listed n the Foreign Patent Documents section of this IDS.

Lifewarmer; Applicant's Response to First Office Action, dated Aug. 20, 2019, in parent U.S. Appl. No. 15/557,006, filed Sep. 8, 2017.

USPTO; Second Office Action, dated Nov. 18, 2019, in parent U.S. Appl. No. 15/557,006, filed Sep. 8, 2017.

Smiths Medical; "Level 1 Hotline [TM] Blood and Fluid Warmer"; Copyright 2019.

Lifewarmer; Applicant's Response to Second Office Action, dated Feb. 12, 2020, in parent U.S. Appl. No. 15/557,006, filed Sep. 8, 2017.

USPTO; Third Office Action, dated Mar. 10, 2020, in parent U.S. Appl. No. 15/557,006, filed Sep. 8, 2017.

Lifewarmer; Applicant's Response to Third Office Action, dated May 15, 2020, in parent U.S. Appl. No. 15/557,006, filed Sep. 8, 2017.

USPTO; Notice of Allowance, dated Jun. 2, 2020, in parent U.S. Appl. No. 15/557,006, filed Sep. 8, 2017.

Thermal Angel; "Thermal Angel (TA-200)" retrieved on Oct. 28, 2014 from http://www.thermalangel.com.

Thermal Angel; "Comparison", retrieved on Oct. 28, 2014 from http://www.thermalangel.com.

Ecourses; "Ch. 4 Beam Stresses", retrieved on Mar. 15, 2019 from http://www.ecourses.ou.edu.

Dubick, et al; "Evaluation of Commercially Available Fluid-Warming Devices for Use in Forward Surgical and Combat Areas"; Military Medicine, vol. 170, Jan. 2005.

Texas Instruments; "Measurement error caused by self-heating in NTC and PTC thermistors", Analog Design Journal third quarter, 2019, pp. 1-7.

TDK; "Temperature protection devices; Chip NTC thermistor; NTCG series"; Dec. 2017.

Gaymar Industries; "Medi-Temp III REF FW600 Blood/Fluid Warmer"; retrieved on Oct. 4, 2019 from https://techweb.stryker.com.

Smiths Medical; "Operator's Manual Level1 Hotline Blood and Fluid Warmer"; retrieved on Oct. 4, 2019 from http://www.smiths-medical.com.

General Electric; "enFlow [TM] IV Fluid / Blood Warmer"; copyright 2009.

Arizant Healthcare; "Operator's Manual Model 245 SmarHeat* Ranger Blood/Fluid Warming"; Copyright 2009.

Sensor Scientific, Inc.; "Understanding the self heating effect of NTC thermistors"; copyright Jun. 23, 2019.

International Searching Authority (EPO); "Written Opinion of the International Searching Authority"; in the parent international patent application PCT/US2016/021795.

International Searching Authority (EPO); "International Search Report"; in the parent International patent application PCT/US2016/021795.

Simscale; "Electronics Cooling Multiphysics Simulation: Simulate early, simulate more, simulate now with SimScale" Retrieved on Nov. 30, 2022 from https://www.simscale.com/electronics-cooling-multiphysics-simulation/.

* cited by examiner

FIG. 11B TEMPERATURE MEASUREMENT
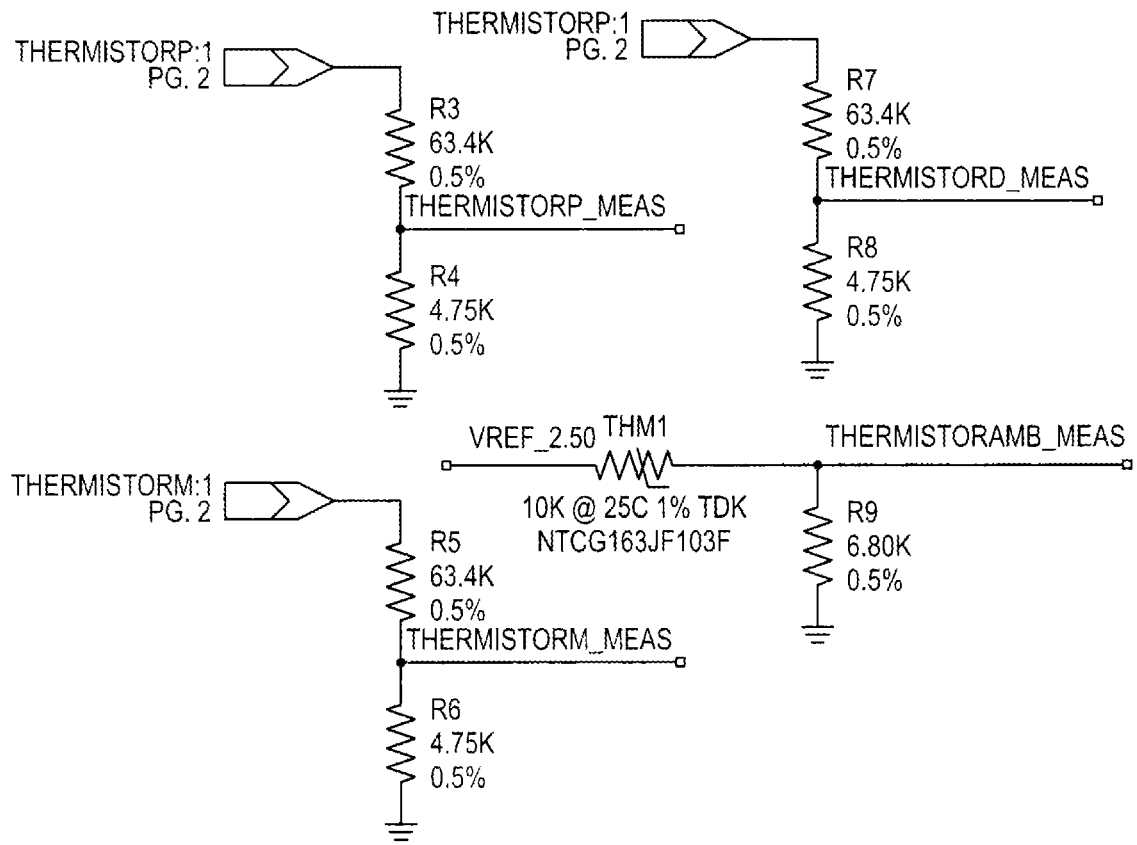
FIG. 11C BATTERY MEASUREMENT
$$V_{IN} = [(210K + 10.5K) * V_{REF} * ADC] / [2^{12} * 10.5K]$$
$$= ADC * 0.012817383 \text{ (V)}$$
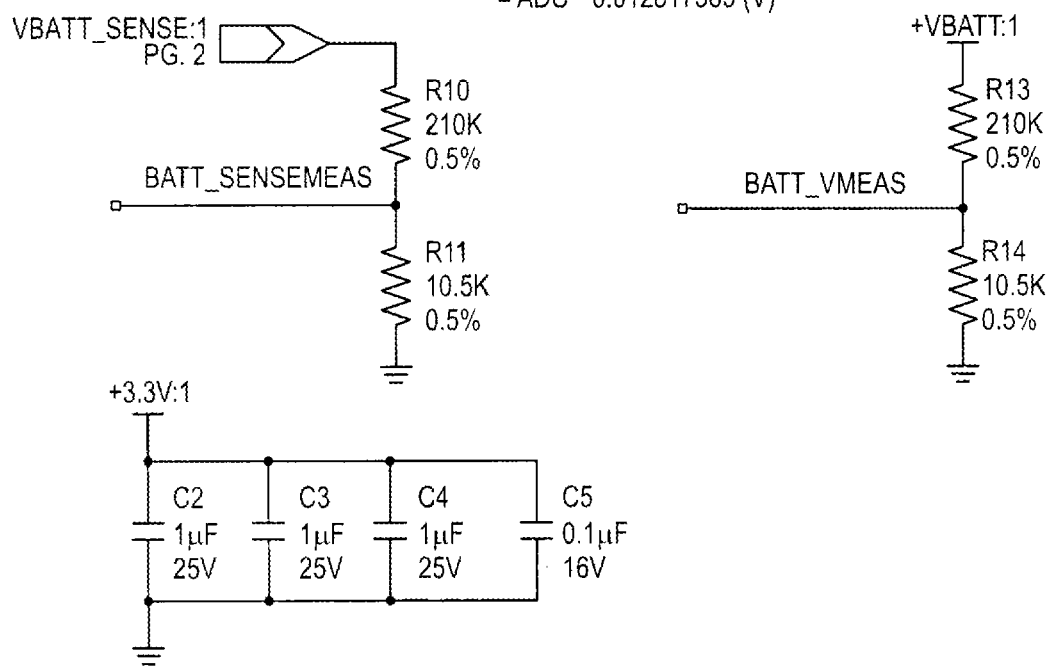

THERMIC INFUSION SYSTEM DRY TUBE DETECTOR

CROSS-REFERENCE TO RELATED APPLICATIONS (CLAIMING BENEFIT UNDER 35 U.S.C. 120)

This is a continuation-in-part of U.S. patent application Ser. No. 15/557,006, filed on Sep. 8, 2017, which was a U.S. National Stage application filed under 35 U.S.C. § 371 of International Application No. PCT/US16/21795, filed Mar. 10, 2016, now U.S. Pat. No. 10,780,258, which claimed priority under 35 U.S.C. § 119(e) from U.S. provisional application No. 62/196,881, filed Mar. 10, 2015, all by applicant Life Warmer Inc. of Canton, CT, USA.

FEDERALLY SPONSORED RESEARCH AND DEVELOPMENT STATEMENT

None.

MICROFICHE APPENDIX

Not applicable.

INCORPORATION BY REFERENCE

The entire contents of the above-referenced patent application is hereby expressly incorporated herein by reference in its entirety.

BACKGROUND

Hypothermia occurs when the body's core temperature drops below 35 degrees Celsius due to extreme exposure to cold, decrease in heat production, or increase in heat loss. It is a generally understood physiological fact that nearly one hundred percent of all trauma patients that reach a core temperature of 32 degrees Celsius or less will die. Trauma patients also generally cool quickly due to a number of factors, and such cooling leads to what is known as the "triad of death": hypothermia, acidosis, coagulopathy.

Warming of intravenous fluid (e.g., blood) is a critical early intervention technique that may decrease mortality and morbidity related events due to hypothermia. By providing a patient with warmed blood or other resuscitative fluids through an intravenous device, a more favorable prognosis may be achieved.

Portability of the intravenous device may further aid in the early prevention of hypothermia—i.e., the trauma patient is provided with warmed fluid at the scene of the trauma and in a more immediate manner. Currently within the art, infusion fluid heaters primarily use a serpentine path between heating elements, flow into a rectangular geometry cartridge space expanding surface area contact with a heating element, and/or provide heating elements within a bath of fluid. These devices are bulky, cumbersome, and require multiple components and are challenging to set up. As such, portability of the infusion fluid heaters within the field is limited.

In warming blood, hemolysis also becomes a concern as the blood must remain below a certain temperature in order to prevent hemolysis. As flow through intravenous devices is generally laminar, blood positioned near the inner wall of the intravenous device may reach the temperature of the inner wall. Placement of a heating element in contact with the inner wall raises hemolysis concerns and has generally been avoided in the art. Even further, current inline blood warmers within the art typically place shear forces on a fluid as the fluid flows from infusion tubing into a cartridge and outflows via a tubing to the patient. Additionally, the flow dynamics change from laminar to transitional and turbulent during this process. Increased shear forces and non-laminar flow is known to damage membranes of red blood cells affecting distensibility and impairing the function of transfused blood to oxygenate tissue in the microcirculation.

Therefore, there is a need in the art for new and improved laminar flow infusion systems that can safely regulate the temperature of fluid while providing portability of the device within the field.

BRIEF DESCRIPTION OF THE DRAWINGS

These and other objects and features of the present invention will be more fully disclosed or rendered obvious by the following detailed description of the invention, which is to be considered together with the accompanying drawings wherein like numbers refer to like parts, and further wherein:

FIGS. 11A-11D illustrate schematic circuit diagrams of an exemplary control system for use in the in thermic infusion system of FIG. 1A.

DETAILED DESCRIPTION OF EXEMPLARY EMBODIMENT(S)

Figure 1A:
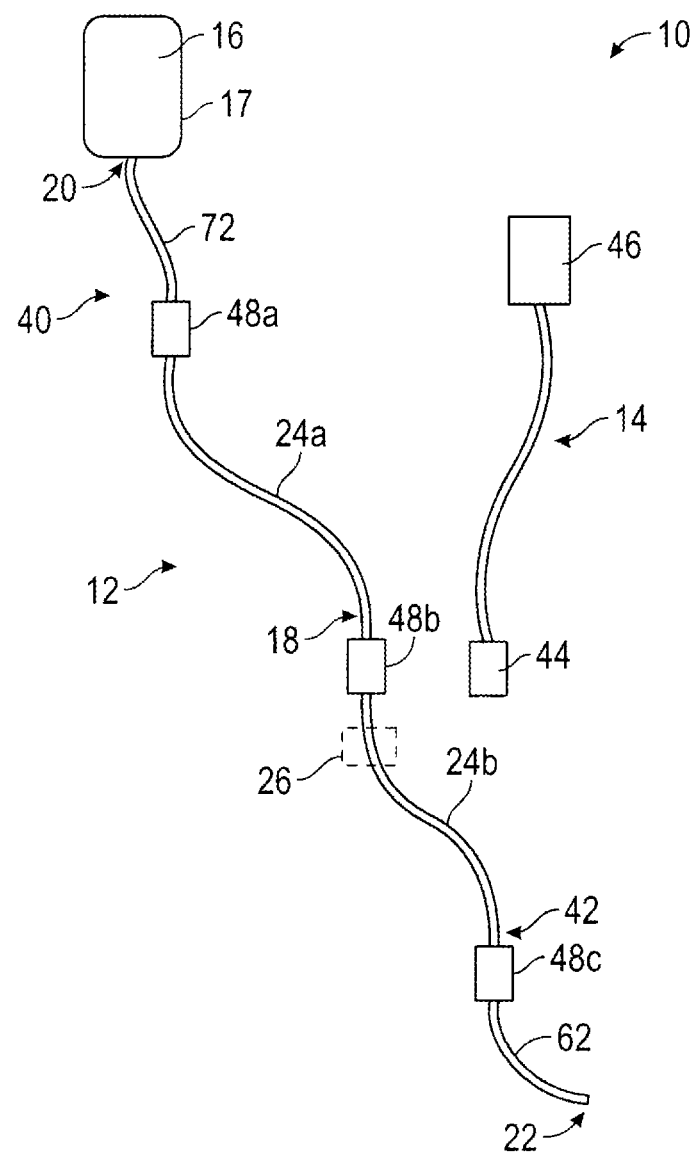
FIG. 1A is a diagrammatic view of a thermic infusion system constructed in accordance with the present disclosure.

Before explaining at least one embodiment of the presently disclosed and claimed inventive concepts in detail, it is to be understood that the presently disclosed and claimed inventive concepts are not limited in their application to the details of construction, experiments, exemplary data, and/or the arrangement of the components set forth in the following description or illustrated in the drawings. The presently disclosed and claimed inventive concepts are capable of other embodiments or of being practiced or carried out in various ways. Also, it is to be understood that the phraseology and terminology employed herein is for purpose of description and should not be regarded as limiting.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, certain well-known features may not be described in detail in order to avoid unnecessarily complicating the instant disclosure.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements but may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

The term "and combinations thereof" as used herein refers to all permutations or combinations of the listed items preceding the term. For example, "A, B, C, and combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. A person of ordinary skill in the art will understand that typically there is no limit on the number of items or terms in any combination, unless otherwise apparent from the context.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

The use of the terms "at least one" and "one or more" will be understood to include one as well as any quantity more than one, including but not limited to each of, 2, 3, 4, 5, 10, 15, 20, 30, 40, 50, 100, and all integers and fractions, if applicable, therebetween. The terms "at least one" and "one or more" may extend up to 100 or 1000 or more, depending on the term to which it is attached; in addition, the quantities of 100/1000 are not to be considered limiting, as higher limits may also produce satisfactory results.

Further, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein qualifiers such as "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, and combinations thereof, for example.

As used herein, the term "patient" is meant to include all organisms, whether alive or dead. For example, a method according to the inventive concepts disclosed herein may be used to regulate fluid temperature for infusion into a living human, horse, cow, sheep, cat, dog, and the like. In another example, a method according to the inventive concepts disclosed herein may be used in a non-living organism to train medical personnel, for example.

Although the following disclosure relates to the medical field, the thermic infusion device using different dimensions and optimizations may be used to efficiently heat and/or cool flowing fluid or gas to a safe operating temperature, over a range of flow rates. For example, applicable industry uses may include, petrochemical, chemical processing, pharmaceutical processing, food processing and the like.

Certain exemplary embodiments of the invention will now be described with reference to the drawings. In general, such embodiments relate to thermic infusion systems and methods.

Referring to FIG. 1A, a thermic infusion system 10 is illustrated. Generally, the thermic infusion system 10 includes a thermal tubing system 12 and a control system 14. The thermic infusion system 10 may generally aid in controlling the temperature of an infusion fluid, such as infusion fluid 16 which may be, by way of illustration and not by limitation, blood, plasma, or other infusates. For example, in some embodiments, controlling the temperature of the infusion fluid 16 may include controlling the temperature of the infusion fluid 16 to a physiological beneficial temperature range (e.g., between approximately 35-39 degrees Celsius). In some embodiments, controlling the temperature of the infusion fluid 16 may include controlling the temperature of the infusion fluid 16 to a pre-set temperature range (e.g., between approximately 37-41 degrees Celsius). In some embodiments, controlling the temperature of the infusion fluid 16 may include controlling the temperature of the infusion fluid 16 over a range of flow rates (e.g., 2-50 m L/m in) and/or ambient conditions. In some embodiments, the thermic infusion system 10 may maintain fluid below a potentially detrimental temperature (e.g., temperature wherein hemolysis occurs), for example.

Referring to the thermal tubing system 12 shown in FIG. 1A, controlling the temperature range of the infusion fluid 16 may include using heating and/or cooling elements embedded in or contacting the thermal tubing system 12. In some embodiments, the thermal tubing system 12 may substitute for a standard infusion line as known by one skilled in the art.

Figure 1B:
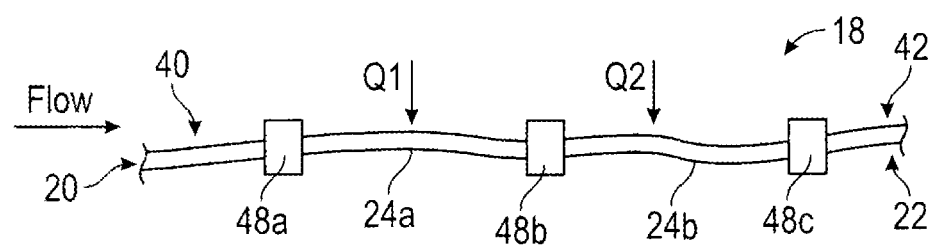
FIG. 1B is a diagrammatic view of heat transfer through the thermic infusion system illustrated in FIG. 1A.
Figure 2:
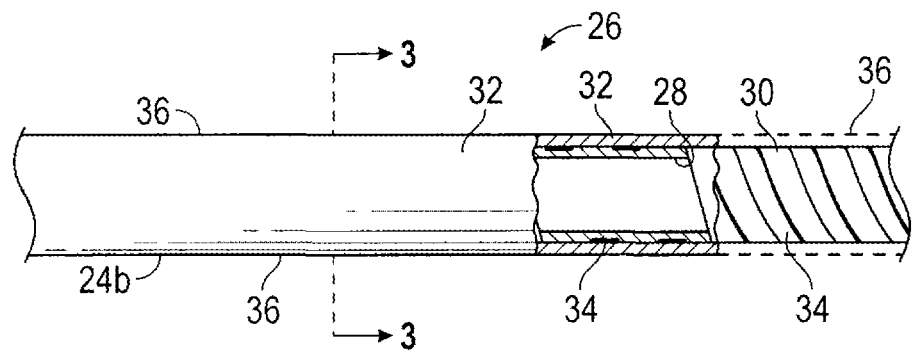
FIG. 2 is an exemplary embodiment of a portion of a tubal segment for use in the thermic infusion system of FIG. 1A. A portion of the tubal segment is illustrated in a cross sectional view and a portion of the tubal segment is illustrated with an outer sheath of the tubal segment removed such that a thermal element of the tubal segment is viewed.
Figure 3:
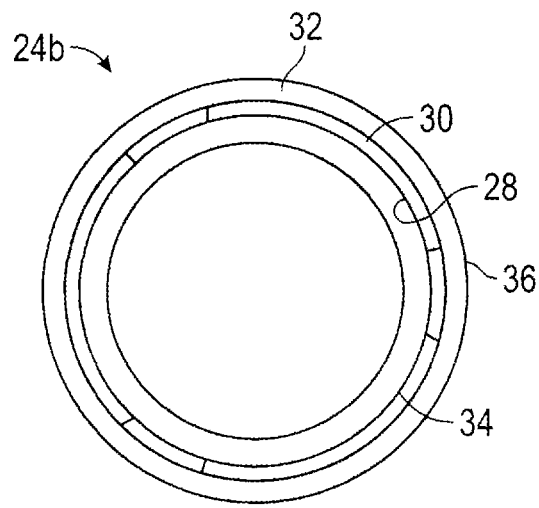
FIG. 3 is a cross sectional view of the tubal segment illustrated in FIG. 2 taken along line 3-3.

Referring to FIGS. 1-3, the thermal tubing system 12 includes a tubal body 18 having an inlet port 20 and an outlet port 22. The inlet port 20 may connect to a source 17 for the infusion fluid 16 such that fluid may flow into the inlet port 20 and through the tubal body 18 and out of the outlet port 22 to a patient. For example, the source 17 of the infusion fluid 16 may be an infusion bag as is known within the art. In some embodiments, elements such as a drip chamber, injection port, roller clamp, slide clamp, and/or the like may be positioned adjacent to the inlet port 20, tubal body 18, and/or source 17 of the infusion fluid 16. Such elements are well known to a person skilled within the art and need no further description herein. The outlet port 22 may connect to a cannula, and/or the like for insertion into the patient such that the infusate may flow to the patient. In some embodiments, the tubal body 18 may be disposable.

In some embodiments, the tubal body 18 may be configured such that there is limited or no change in the geometry therethrough. For example, in some embodiments, the tubal body 18 may be configured to be at a substantially similar diameter therethrough. Such limited change in the geometry may provide for laminar flow of the infusion fluid 16 through the tubal body 18.

The flow pattern of the infusion fluid 16 through the thermal tubing system 12 may be laminar and occur at a Reynolds Number (Re) below 2000, known as the critical number. For example, the Re may be approximately 300 to 600. As such, in some embodiments, flow conditions of the infusion fluid 16 through substantially all of the thermal tubing system 12 may result in a Reynolds number no greater than 1000. In some embodiments, flow conditions of the infusion fluid 16 through substantially all of the thermal tubing system 12 may result in a Reynolds number no greater than 750. In some embodiments, flow conditions of the infusion fluid 16 through substantially all of the thermal tubing system 12 may result in a Reynolds number no greater than 600. In some embodiments, flow conditions of the infusion fluid 16 through substantially all of the thermal tubing system 12 may result in a Reynolds number no greater than 500. In some embodiments, flow conditions of the infusion fluid 16 through substantially all of the thermal tubing system 12 may result in a Reynolds number no greater than 400. In some embodiments, flow conditions of the infusion fluid 16 through substantially all of the thermal tubing system 12 may result in a Reynolds number no greater than 350.

Additionally, configuration of the thermal tubing system 12 may be such that calculated shear force of the thermal tubing system 12 associated with infusion fluid 16 flowing therethrough is less than maximum physiological shear stress within the human vascular system (i.e., 10 Pa). For example, in some embodiments, the calculated shear force may be between approximately 4 Pa to 9 Pa. In some embodiments, the calculated shear force through substantially all of the thermal tubing system 12 may be less than 9 Pa. In some embodiments, the calculated shear force through substantially all of the thermal tubing system may be less than 8 Pa. In some embodiments, the calculated shear force through substantially all of the thermal tubing system may be less than 7 Pa. In some embodiments, the calculated shear force through substantially all of the thermal tubing system may be less than 6 Pa. In some embodiments, the calculated shear force through substantially all of the thermal tubing system may be less than 5 Pa. In some embodiments, the calculated shear force through substantially all of the thermal tubing system may be less than 5.5 Pa.

The tubal body 18 may include one or more tubal segments 24. For example, FIG. 1A illustrates the tubal body 18 having two tubal segments 24a and 24b. Each tubal segment 24a and 24b may have similar or different lengths. Any number of tubal segments 24 may be included within the tubal body 18. Each tubal segment 24a and 24b may provide heat transfer (e.g., heating/cooling) to the infusion fluid 16 flowing through the tubal body 18. Generally, formation of the tubal segments 24 are such that electrical energy may be converted for heat transfer (e.g., heating, cooling), such that the temperature of the infusion fluid 16 may be affected (e.g., raised, lowered, stabilized).

FIG. 2 illustrates a portion 26 of the tubal segment 24b of FIG. 1A. For simplicity in description, the tubal segment 24b is described in further detail here; however, it should be appreciated by one skilled in the art that the tubal segment 24a may contain the same elements described in relation to tubal segment 24b.

Generally, the tubal segment 24b may be configured to provide thermal transfer of heat (e.g., heating/cooling) to the infusion fluid 16. In some embodiments, the tubal segment 24b may provide the feel and/or handling characteristics of conventional intravenous (IV) tubing known within the art. In some embodiments, the tubal segment 24b may be configured to be resistant to kinking when coiled for packaging and/or when handled in use. In some embodiments, if a kink in the tubal segment 24b occurs, the tubal segment 24b may rebound from such kink. In some embodiments, the tubal segment 24b may provide visibility of the fluid path of the infusion fluid 16 through the tubal body 18. As a person skilled in art is aware, in patient care settings, standard infusion tubing routinely kinks and is crushed. The tubal body 18, and in particular the tubal segments 24a and 24b may configured to be kink resistant and crush resistant as described in further detail herein.

Referring to FIGS. 1-4, the tubal segment 24b, as also applied to the tubal segment 24a, includes an inner sheath 28, a thermal element 30, and an outer sheath 32. In some embodiments, the inner sheath 28 may be formed of more rigid material(s) as compared to the outer sheath 32 such that kinking and/or crushing of the tubal segment 24b may be reduced and/or prevented. Additionally, the materials selected for the inner sheath 28 and/or the outer sheath 32 may be configured such that rebound may occur in a kinking and/or crushing event. During rebound, it should be noted that flow of the fluid through the tubal body 18 may continue and not be impeded. In some embodiments, the ratio of thickness of the inner sheath 28 as compared to the outer sheath 32 may be configured such that kinking and/or crushing of the tubal segment 24b may be reduced and/or prevented, and/or rebound after a kinking and/or crushing event may occur. For example, the inner sheath 28 may have a thickness of approximately 0.15 mm and the outer sheath 32 may have a thickness of approximately 0.39 mm.

The inner sheath 28 may be configured as a hollow cylindrical body for conveying infusion fluid 16 therethrough. The inner sheath 28 may be formed of any flexible, biocompatible material including, but not limited to, one or more extrudable polymers, polyurethane, one or more thermoplastic elastomers, Elastollan, fluorinated ethylene propylene (FEP) and/or the like, for example. Generally, the material of the inner sheath 28 may provide for heat transfer from the thermal element 30 to the infusion fluid 16 traveling through the tubal body 18. In some embodiments, the inner sheath 28 may be formed of a completely or intermittently clear (e.g., translucent, transparent, or the like) material. In some embodiments, the inner sheath 28 may be formed of a completely or intermittently opaque material.

In some embodiments, a tie layer 34 may optionally be positioned between the inner sheath 28 and the thermal element 30. The tie layer 34 may be a thin layer configured to stabilize the thermal element 30. The tie layer 34 may be formed of any flexible, biocompatible material, including, but limited to, polyvinyl chloride (PVC), polyurethane, Pellethane, Pebax, and/or the like, for example. In some embodiments, the tie layer 34 may be used to prevent slippage of the thermal element 30 during handling. In some embodiments, the tie layer 34 may be formed of clear (e.g., transparent, translucent, and/or the like) material.

The thermal element 30 is configured to convert energy (e.g., electrical energy) into heat to propagate heat transfer (e.g., cooling or heating) to the infusion fluid 16. For example, heat from the thermal element 30 may be transferred through the inner sheath 28 and the tie layer 34 to the infusion fluid 16 flowing through the tubal segment 24b. In some embodiments, the thermal element 30 may be formed of conductive materials including, but not limited to, copper, nickel, cuprothol, silver, gold aluminum, molybdenum, tungsten, zinc, palladium, nichrome, other suitable alloys, and/or the like, for example. In some embodiments, the thermal element 30 may be formed of a plurality of materials woven into a ribbon formation, solid circular wire, ribbon with a substantially rectangular cross section, and/or any other cross sectional configuration (e.g., fanciful). In some embodiments, the thermal element 30 may be formed of a flexible Peltier element, or other element such that the thermal element 30 may both heat and cool the infusion fluid 16 flowing through the tubal segment 24b.

The thermal element 30 may be positioned adjacent to the inner sheath 28 or the tie layer 34. In some embodiments, the thermal element 30 may extend the entire length of the tubal segment 24b. In some embodiments, the thermal element 30 may extend a portion of the tubal segment 24b.

Figure 4:
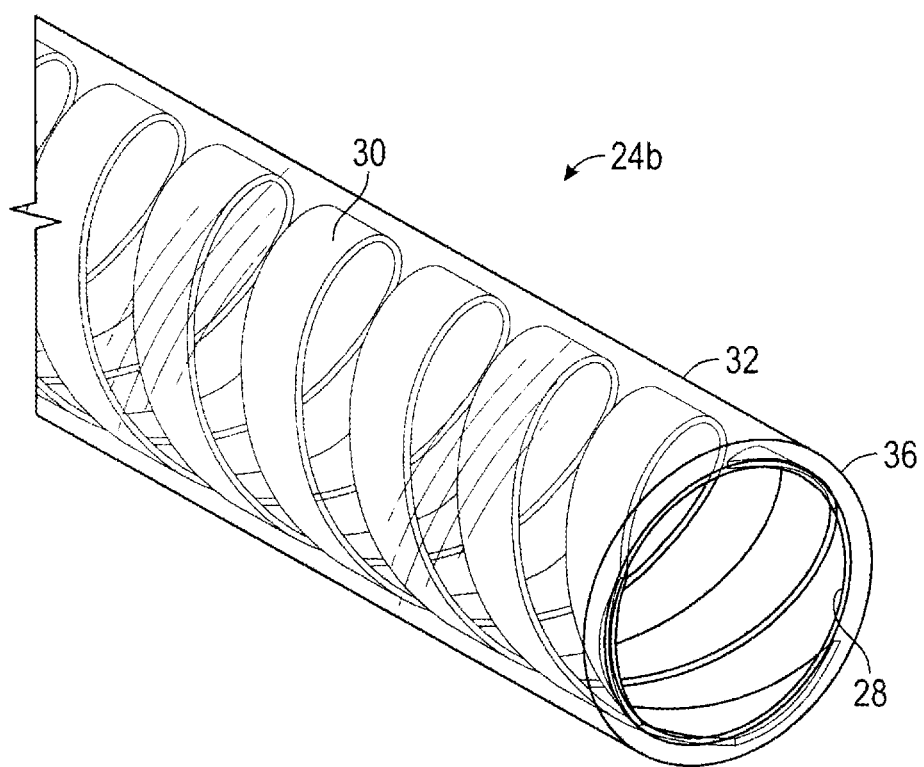
FIG. 4 is a perspective view of an exemplary tubal segment for use in the thermic infusion system of FIG. 1A.

In some embodiments, the thermal element 30 may cover the entire inner sheath 28. In some embodiments, the thermal element 30 may cover a portion of the inner sheath 28. For example, as illustrated in FIGS. 2 and 4, in some embodiments, the thermal element 30 may be provide in a helical-type configuration (e.g., single helix, double helix, triple helix, and/or the like) around the inner sheath 28 and tie layer 34 covering a portion of the inner sheath 28. For example, in some embodiments, the thermal element 30 may be configured as a triple helix formed as a ribbon of cuprothol and/or silver plated copper wire. In another example, the thermal element 30 may be configured as a double helix formed as a ribbon of nichrome.

Pitch of the thermal element 30 about the inner sheath 28 may be configured to reduce kinks, crushing, and/or aid in rebound of the tubal segment 24b. For example, in some embodiments, the pitch of the thermal element 30 about the inner sheath 28 may be approximately 6.3 mm/revolution.

In some embodiments, each tubal segment 24a and 24b may include differential energy transfer capabilities. For example, the tubal segment 24a positioned near the inlet port 20 may have greater energy transfer capabilities as compared to the tubal segment 24b positioned near the outlet port 22. As such, each tubal segment 24a and 24b may be formed of different materials and/or have different configurations such that differential energy transfer capabilities may be provided.

The outer sheath 32 may be formed of a material configured to reduce and/or prevent thermal energy loss. For example, the outer sheath 32 may be formed of a material configured to reduce and/or prevent thermal energy loss to an ambient environment. Such material may include, but is not limited to, polyurethane, Pellethane, and/or the like, for example. Additionally, in some embodiments, the material of the outer sheath 32 may be configured to electrically insulate the thermal element 30. The material of the outer sheath 32 may also be configured such that an outer surface 36 of the outer sheath 32 remains at a temperature well below that which produces any kind of burn. In some embodiments, the outer sheath 32 may be formed of completely or intermittently clear (e.g., translucent, transparent, or the like) material. In some embodiments, the outer sheath 32 may be formed of a completely or intermittently opaque material.

Referring to FIGS. 1-2, the control system 14 may modulate and/or regulate energy to the tubal segments 24a and 24b, and more particularly, to the thermal elements 30 of the tubal segments 24a and 24b. By modulating and/or regulating energy to the tubal segments 24a and 24b, temperature of the infusion fluid 16 may be controlled. FIGS. 11A-11D illustrate schematic diagrams of an exemplary control system 14a for use in the thermic infusion system of FIG. 1A. In some embodiments, the control system 14a may also include a temperature measurement system, a battery measurement system, and/or a status indicator system.

In some embodiments, each thermal element 30 of each tubal segment 24a and 24b may be controlled individually. As such, the control system 14 may be configured to control the temperature of the infusion fluid 16 flowing through the tubal body 18 by individually optimizing heat delivered through each tubal segment 24a and 24b. The thermic infusion system 10 may thus provide individually controlled tubal segments 24a and 24b configured to control fluid temperature of the infusate flowing therethrough to a predefined temperature (e.g., below hemolysis threshold).

Referring to FIG. 1B, in some embodiments, the control system 14 may provide a greater transfer of heat to the infusion fluid 16 flowing through the tubal segment 24a positioned at a proximal end 40 of the tubal body 18 as compared to the transfer of heat provided to the infusion fluid 16 flowing through the tubal segment 24b positioned at a distal end 42 of the tubal body 18. For example, a first amount of heat $Q_1$ may be provided to the tubal segment 24a and a second amount of heat $Q_2$ may be provided to the tubal segment 24b. The first amount of heat $Q_1$ may be greater than the second amount of heat $Q_2$ or, alternatively, the first amount of heat $Q_1$ may be less than the second amount of heat $Q_2$.

Figure 5:
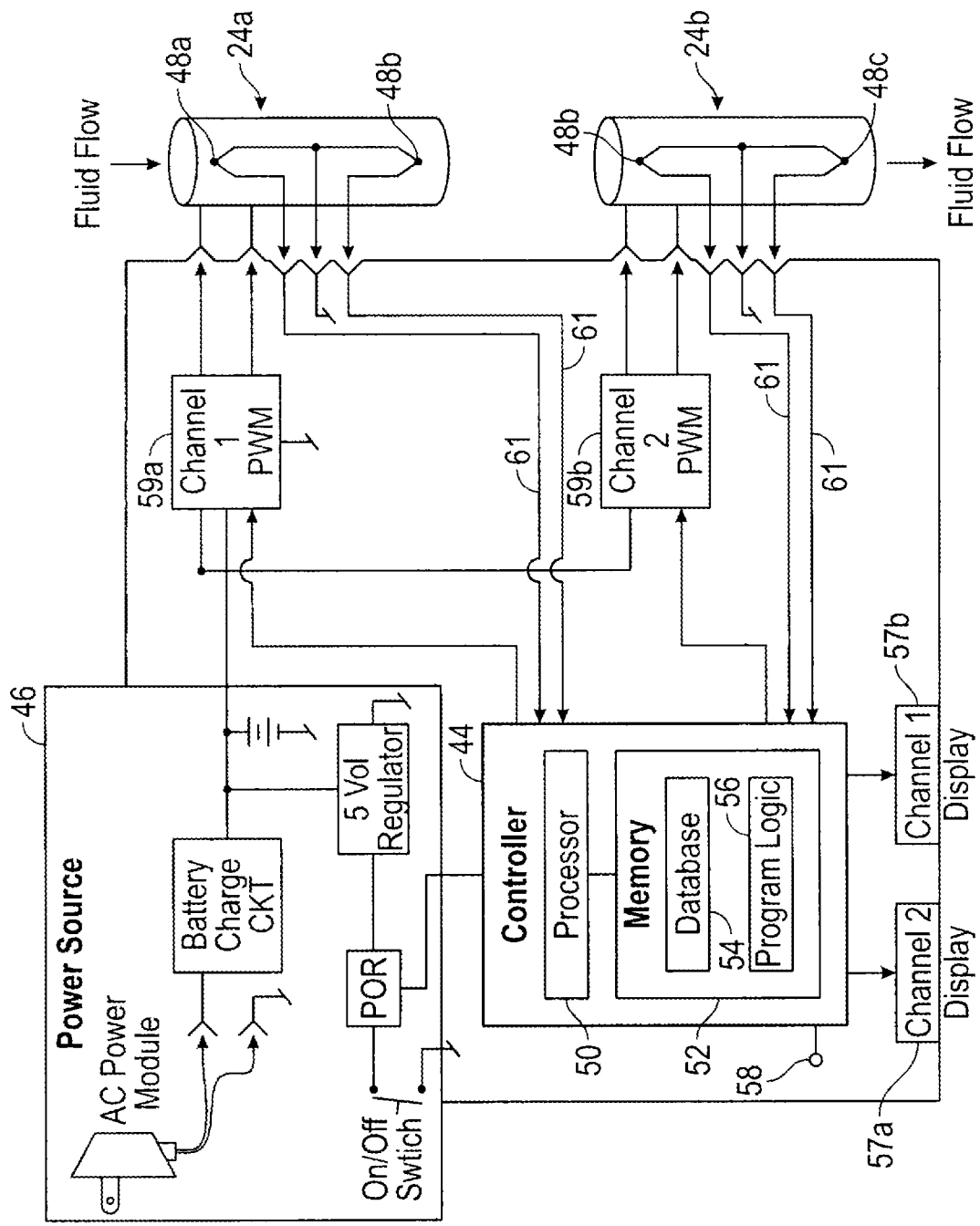
FIG. 5 is a block diagram of an exemplary control system and power supply for use in the thermic infusion system of FIG. 1A.

Referring to FIGS. 1, 2 and 5, the control system 14 may include a control unit 44, a power source 46, and one or more sensors 48. Generally, the control unit 44 may utilize data obtained by the one or more sensors 48 to determine the amount of heat Q to be provided to one or more tubal segments 24. In some embodiments, heat Q may be provided to the tubal segments 24 in the form of electrical energy supplied to the thermal elements 30. The one or more sensors 48 provide a signal to the control unit 44 indicative of the temperature of the infusion fluid 16 as it flows through the tubal body 18. The control unit 44 may utilize a control algorithm and data provided by the one or more sensors 48 to modulate energy (e.g., electrical energy) to the thermal elements 30 of the tubal segments 24a and 24b. In some embodiments, each thermal element 30 may be controlled individually.

In some embodiments, communication between the control unit 44 and multiple sensors 48 may provide a safety feedback control. For example, one or more sensors 48 may be positioned in communication with the infusion fluid 16 such that failure of one or more sensors 48 may provide a signal to the control unit 44. The control unit 44 may determine to continue operation, reduce operation or turn off. Such safety feedback control may maintain a safe fluid environment (e.g., temperature, flow).

The control unit 44 comprises one or more processors 50 capable of executing processor executable code and one or more non-transitory memory 52 capable of storing processor executable code. The processor executable code causes the processor 50 to receive data from the one or more sensors 48; analyze the data received from the sensors 48; and, provide electrical energy to the tubal segments 24a and 24b, and more particularly, to the thermal elements 30 of the tubal segments 24a and 24b based on the analysis of the data. Any suitable technique may be used to interpret the data received from the sensors 48. For example, the processor executable code may be configured to utilize techniques and/or algorithms known within the art (e.g., proportional/integral/derivative (PID) control, hierarchical (cascade) control, optimal (model predictive) control, intelligent (fuzzy logic) control, adaptive control, and/or the like).

The processor 50 may be implemented as a single processor or multiple processors working together to execute the logic described herein. Each processor 50 may be capable of reading and/or executing code and/or capable of creating, manipulating, retrieving, altering and/or storing data structure. Exemplary embodiments of the one or more processors 50 include, but are not limited to, digital signal processors (DSPs), central processing units (CPUs), field programmable gate arrays (FPGAs), microprocessors, multi-core processors, combinations thereof, and/or the like.

In some embodiments, the one or more processors 50 may be located remotely from one another and use a network protocol to communicate therebetween. To that end, in some embodiments, each element of the control unit 44 may be partially or completely network based, and may not be located in a single physical location (e.g., with a single housing). The network may permit uni-directional or bi-directional communication of information and/or data between the one or more processors 50 and/or the one or memories 52.

The one or more memories 52 may be capable of storing processor executable code and/or information including one or more databases 54 and program logic 56. For example, the database may store data indicative of sensing data provided by the one or more sensors 48. In some embodiments, the processor executable code may be stored as a data structure, such as a database and/or data table, for example. Additionally, the one or more memories 52 may be implemented as a conventional non-transient memory, such as, for example, random access memory (RAM), a CD-ROM, a hard drive, a solid state drive, a flash drive, a memory card, a DVD-ROM, an optical drive, combinations thereof, and/or the like.

The one or more memories 52 may be located in the same physical location as the one or more processors 50 (e.g., in a single housing), or located remotely from the one or more processors 50 and may communicate with the one or more processors 50 via a network, for example. Additionally, when more than one processor 50 is used, one or more memory 52 may be located in the same physical location as the processor 50, and one or more memory 52 may be located in a remote physical location from the processor 50.

The physical location(s) of the one or more memories 52 may be varied. In some embodiments, the one or more memory 52 may be implemented as a "cloud" memory (i.e., one or more memory may be partially, or completely accessed using a network).

Figure 11A:
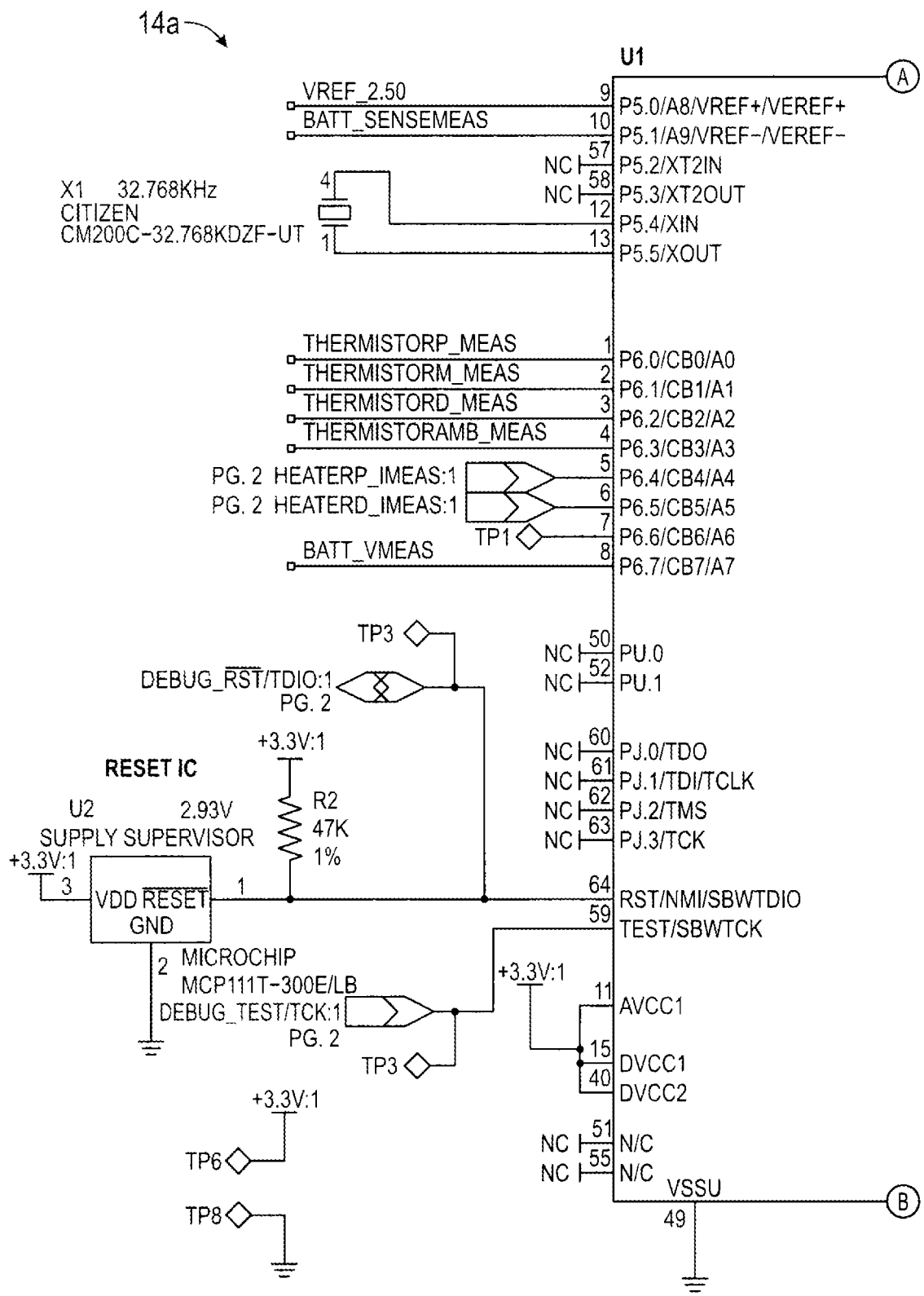
Figure 11A:
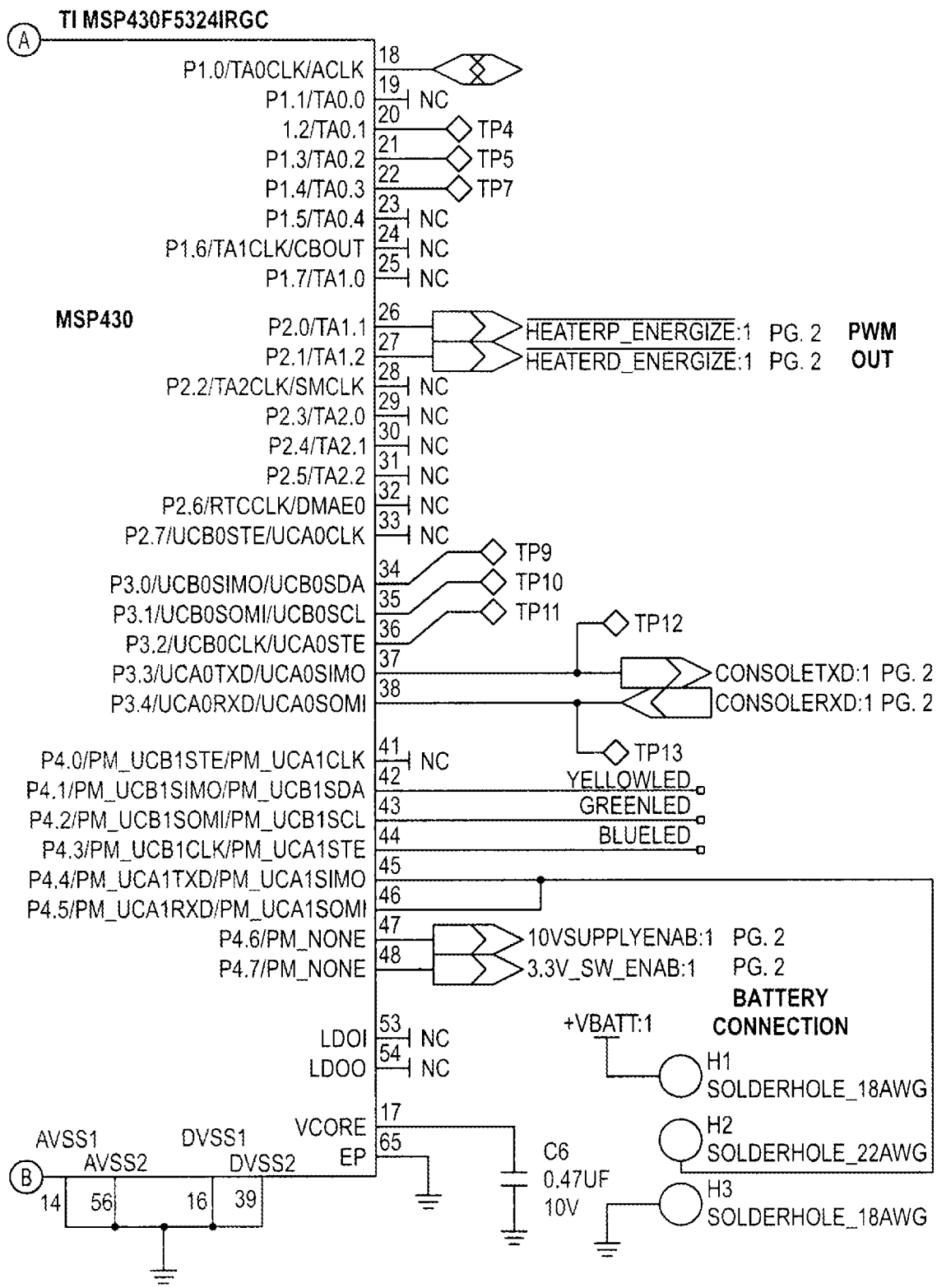
Figure 11D:
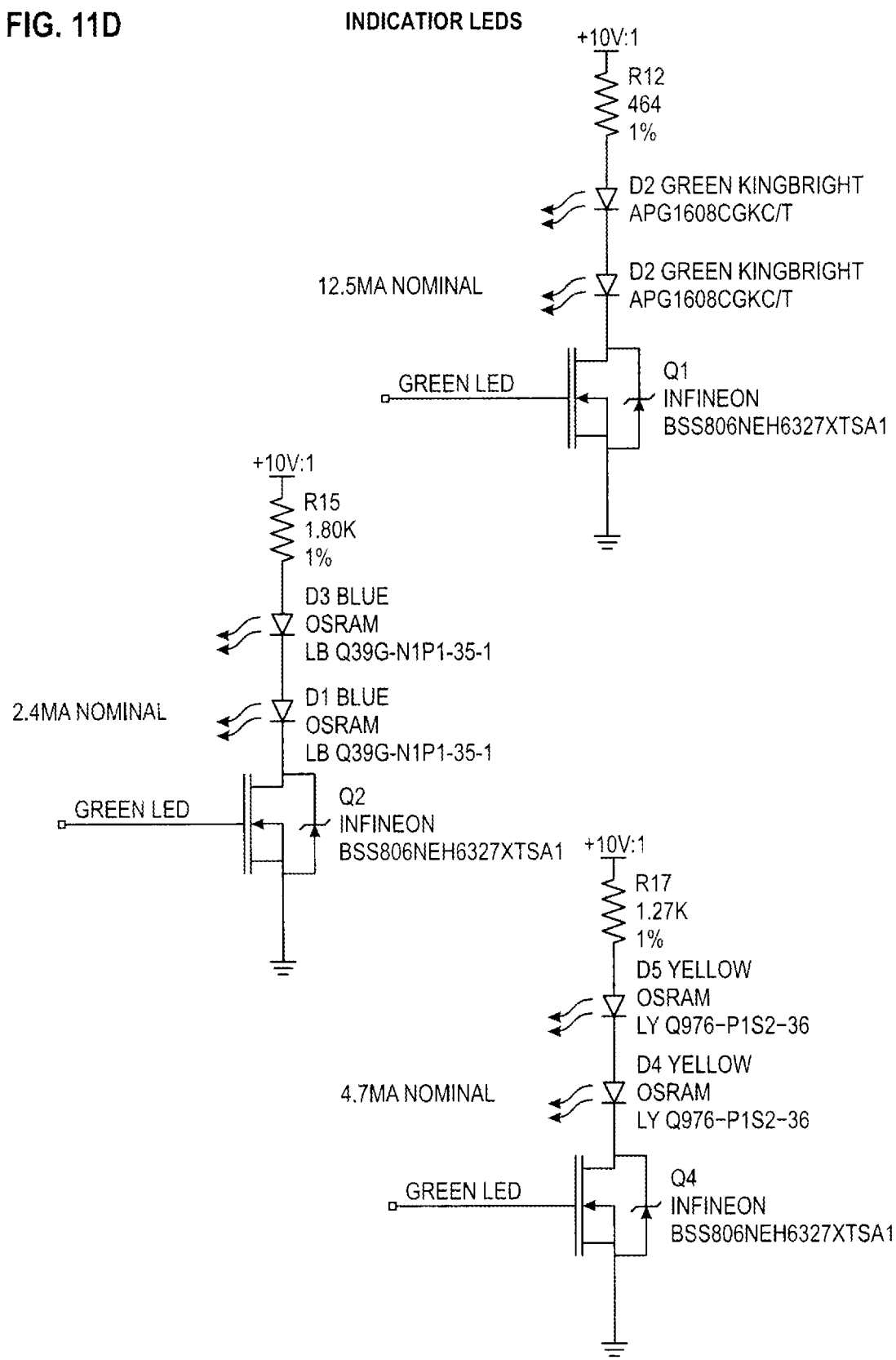

In some embodiments, the control unit 44 may include an output device 57 and an input device 58. The output device 57 of the control unit 44 may transmit information from the processor 50 to a user, such that the information may be perceived by the user. For example, but not by way of limitation, the output device 57 may be implemented as a server, a computer monitor, a cell phone, a tablet, a speaker, a website, a PDA, a fax, a printer, a projector, a laptop monitor, illumination devices, combinations thereof, and/or the like. For example, the output device 57 may include one or more illumination devices (e.g., LEDs) providing one or more status indicators (e.g., temperature reading, status of patient, status of infusion fluid 16, and/or the like). FIG. 5 illustrates the control unit 44 having a first output device 57a providing status indicators related to tubal segment 24a and a second output device 57b providing status indicators related to tubal segment 24b. In some embodiments, the output device 57 may be a cellular telephone wherein the control unit 44 communicates with a user's cellular telephone in providing status indicators, for example. FIG. 11D illustrates another exemplary embodiment wherein a status indicator system may include the use of indicator LEDs (e.g., green, blue and yellow). It should be noted that any number of indicators may be used to provide status indicators as needed. For example, a localized system using indicator LEDs may be provided, as well as, a communication to a cellular telephone and/or the like.

The input device 58 may transmit data to the processor 50 and may be implemented as a keyboard, a mouse, a touch-screen, a camera, a cellular phone, a tablet, a smart phone, a personal digital assistant (PDA), a microphone, a network adapter, a probe having a sensor therein, a microcapillary testing device or array, a microfluidic testing device, combination thereof, and the like.

In some embodiments, the control unit 44 may include a touch screen display forming the output device 57 and the input device 58. The touch screen display may be equipped with a graphical user interface (GUI) capable of communicating information to the user and receiving instructions from the user. Software stored on the one or more memories 52 of the control unit 44 may receive one or more commands (e.g., via the touch screen display) to provide activation of the control unit 44; processing of data according to a defined algorithm stored on the one or more memories 52, displaying received data and/or processed data, and/or monitoring system status and reporting fault conditions, for example.

The control unit 44 controls delivery of energy (e.g., electrical energy) from the power source 46 to the tubal segments 24a and 24b, and more particularly to the thermal element 30 of the tubal segments 24a and 24b shown in FIGS. 1A and 2. In some embodiments, the control unit 44 may control delivery of the energy via one or more channels 59. For example, in FIG. 5, the control unit 44 controls delivery of the energy via a first channel 59a to the tubal segment 24a and a second channel 59b to the tubal segment 24b. In some embodiments, the control unit 44 may automatically sense and/or determine the presence of infusion fluid 16 within the tubal body 18 such that the control unit 44 may begin delivery of the energy based on the presence of infusion fluid 16 within the tubal body 18 (e.g., without other external indicators such as an on/off switch).

The control unit 44 controls delivery of energy from the power source 46 to the tubal segments 24*a* and 24*b*. Referring to FIGS. 1A and 5, the power source 46 may provide energy to the control unit 44, the tubal segments 24*a* and 24*b*, and/or the sensors 48. In some embodiments, the power source 46 may be a battery and/or a power supply. For example, the power source 46 may include, but is not limited to, an integral or external AC/DC converter, primary batteries, rechargeable batteries, solar energy gathering device, an on/off switch, a voltage regulator and/or the like, for example. In some embodiments, the power source 46 may include a bridge such that a communications battery may connect to the power source 46 during field use. Further, in some embodiments, the power source 46 may further include a measurement system providing indications of status (e.g., low, fully charged). For example, FIG. 11C illustrates a battery measurement system for use in the control unit 14.

In some embodiments, the control unit 44 may control delivery of the energy to control the temperature of the infusion fluid 16 such that the temperature of the infusion fluid 16 is at a physiological beneficial temperature range, the temperature of the infusion fluid 16 is at a pre-set temperature range, the temperature of the infusion fluid 16 is based on a range of flow rates and/or ambient conditions, the temperature of the infusion fluid 16 is below a potentially detrimental temperature (e.g., temperature wherein hemolysis occurs), and/or the like, for example.

The control unit 44 utilizes sensing data from the sensors 48 to deliver the energy (e.g., electrical energy) to the tubal segments 24*a* and 24*b*. The sensors 48 may be positioned along the tubal body 18 to obtain and provide fluid measurements (e.g., temperature, flow) of the infusion fluid 16 flowing through the tubal body 18, and transmit such measurements to the control unit 44. In some embodiments, the sensors 48 may communicate the sensing data over one or more communication links 61 (e.g., single communication link, individual communication links or multiple communication links). The sensors 48 may communicate with the control unit 44 uni-laterally or bi-laterally. Transmission over the communication link 61 may be through a wired or wireless connection. The communication link may include one or more of the helical windings, either multiplexed with the thermal element 30, and/or an individual wind. The communication link may be formed of similar material or different material as the thermal element 30. In some embodiments, different conductive material may be selected to optimize performance and/or minimize manufacturing cost.

The sensors 48 may include, but are not limited to, thermistors, thermocouples, resistance temperature detectors (RTDs), flow sensors, pressure sensors, and/or other fluid or gas sensing elements capable of providing sensing data to the control unit 44. For example, in FIG. 11B, the control system 14 indicates the use of multiple thermistors.

In some embodiments, the sensors 48 may sense the flow rate of the infusion fluid 16 and display the flow rate to an operator of the thermic infusion system 10. In some embodiments, the control unit 44 may determine the flow rate using temperature sensing information provided across multiple sensors 48 and the amount of energy provided to the thermal elements 30, for example.

The one or more sensors 48 may be positioned within and/or adjacent to the tubal body 18. For example, FIGS. 1A, 1B and 5 illustrate three sensors 48*a*, 48*b* and 48*c* positioned within the tubal body 18. Although three sensors 48*a*, 48*b* and 48*c* are illustrated, any number of sensors 48 may be used.

Figure 6:
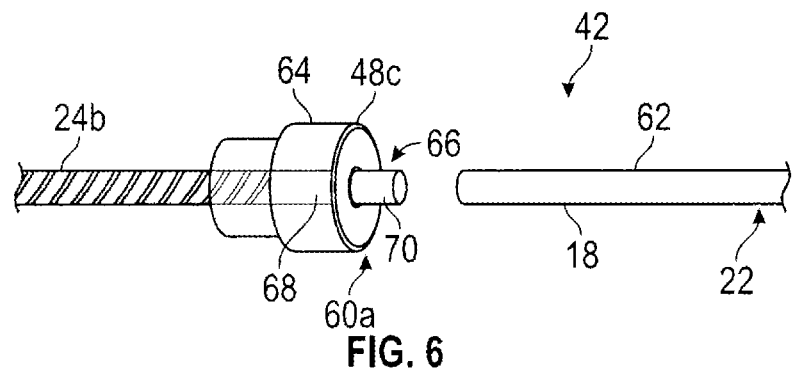
FIG. 6 is a perspective view of an exemplary coupler for use in the thermic infusion system of FIG. 1A.

In some embodiments, the sensors 48 may be integral within the tubal body 18. In some embodiments, one or more couplers 60 may be used to position the sensors 48 within the tubal body 18 such as the exemplary coupler 60*a* illustrated in FIG. 6. FIG. 6 illustrates the distal end 42 of the tubal body 18 in FIG. 1A, having the tubal segment 24*b* connecting to another portion 62 of the tubal body 18. The coupler 60*a* may include a housing 64 and a tubing connector 66. The housing 64 may be formed of materials including, but not limited to, polycarbonate, and/or the like. The sensor 48*c* may be contained within the housing 64 and positioned adjacent to the flow of the infusion fluid 16 such that the sensor 48*c* may sense temperature, flow, and/or the like of the infusion fluid 16. The housing 64 is illustrated in FIG. 6 as cylindrical, however, the housing 64 may be any shape including, but not limited to rectangular, square, oval and/or any fanciful shape.

Figure 10:
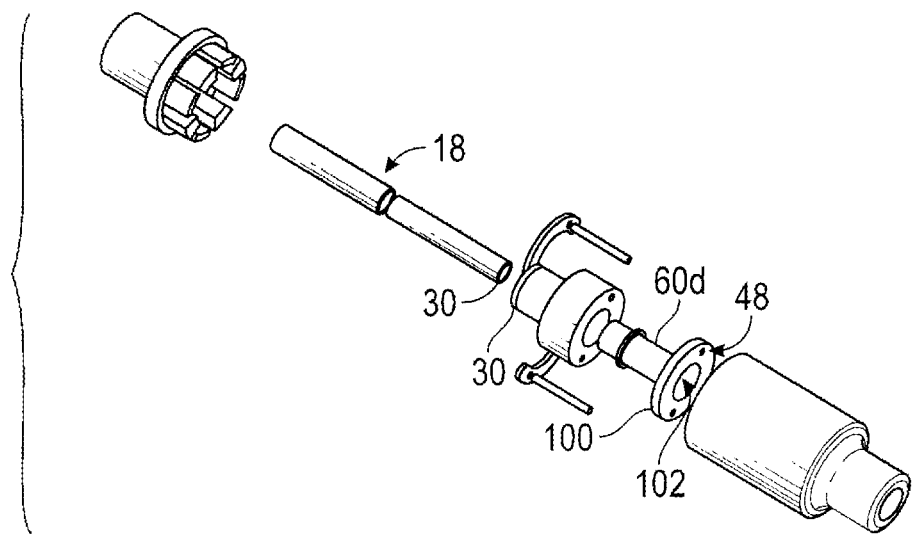
FIG. 10 illustrates an exploded view of an exemplary thermal element in communication with a printed circuit board (PCB) for use in the thermic infusion system of FIG. 1A.

In some embodiments, the sensor 48 may be positioned on a printed circuit board (PCB), wherein the body of the sensor 48 may be positioned in contact with traces that contact a thermally conductive coupler in the tubal body 18 providing for thermal conductivity between the sensor 48 and the infusion fluid 16. For example, FIG. 10 illustrates an exemplary embodiment of a sensor 48 positioned in communication with a PCB 100. In this example, the material of the PCB 100 may minimize thermal conductivity to the thermal elements 30 and/or the tubal body 18 while providing electrical communication and/or connection to the control unit 44 (shown in FIG. 1A) while remaining electrically insulated from the infusion fluid 16 (shown in FIG. 1A). For example, an inner lining 102 of the PCB 100 may be in thermal communication with the sensor 48. In some embodiments, the PCB 100 may have separate traces for thermal conductivity and electrical conductivity. Additionally, the coupler 60*d*, or a portion of the coupler 60*d* may be formed of conductive material.

The tubing connector 66 may be configured to connect to the tubal segment 24*b* and the portion 62 of the tubal body 18. Connection of the tubing connector 66 to the portion 62 of the tubal body 18 may be configured to ensure flow of the infusion fluid 16 therethrough. In some embodiments, the tubing connector 66 may be positioned such that a portion 68 of the tubing connector 66 is within the housing 64 and a portion of the tubing connector 66 is positioned external to the housing 64 as illustrated in FIG. 6. In some embodiments, a polymer or polymer-type mold may be formed to surround the coupler 60*a* to ease the connection for a user and/or stabilize the connection. As one skilled in the art will appreciate, a similar coupler 60*a* may also be used to connect a portion 72 of the tubal body 18 to the tubal segment 24*a* illustrated in FIG. 1A.

Figure 7:
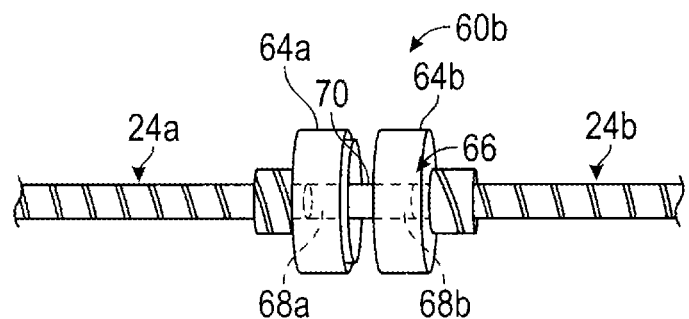
FIG. 7 is a perspective view of another exemplary coupler for use in the thermic infusion system of FIG. 1A.

FIG. 7 illustrates another exemplary embodiment of a coupler 60*b*. The coupler 60*b* may include a first housing 64*a* and a second housing 64*b* connected via the tubing connector 66. A portion 68*a* of the tubing connector 66 may be positioned within the first housing 64*a* and a portion 68*b* of the tubing connector 66 may be positioned within the second housing 64*b* such that between the first housing 64*a* and the second housing 64*b* a portion 70 is external of each of the first housing 64*a* and the second housing 64*b*.

Figure 8:
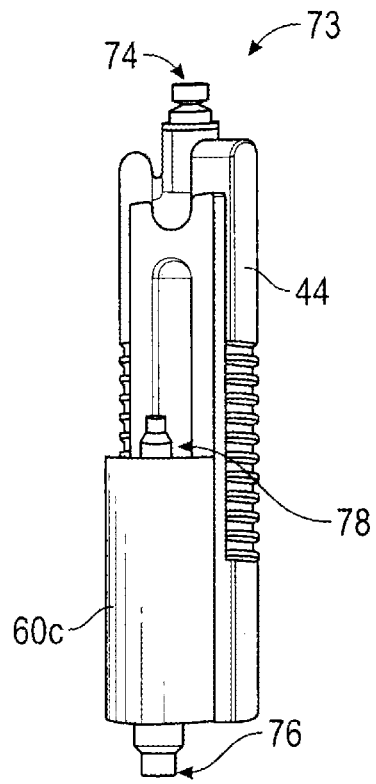
FIG. 8 is a perspective view of an exemplary housing for a control unit for use in the thermic infusion system of FIG. 1A.

FIG. 8 illustrates an exemplary embodiment of a housing 73 for the control unit 44. The housing 73 is illustrated as rectangular, however, the housing 73 may be any shape including, but not limited to, square, oval, cylindrical, and/or any fanciful shape which may, in certain embodiments, reflect the type of infusate for which the control unit is to be used (e.g., the shape of a drop of blood). The housing 73 may include a port 74 for connecting to the power source 46 shown in FIG. 1A. In some embodiments, the housing 73 for the control unit 44 may be positioned adjacent to the coupler 60c as illustrated in FIG. 8. The coupler 60c may include an inflow port 76 and an outflow port 78. In some embodiments, the elements of the coupler 60b illustrated in FIG. 7 may be housed within the coupler 60c.

Figure 9:
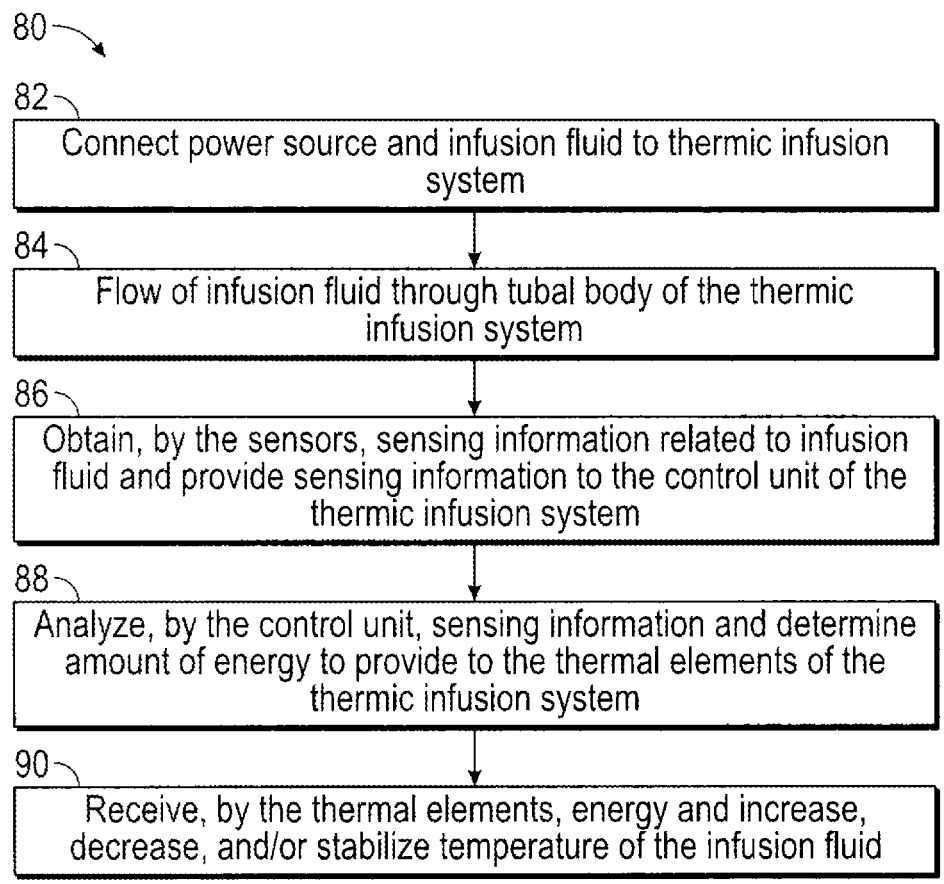
FIG. 9 is a flow chart of an exemplary method for using the thermic infusion system of FIG. 1A.

FIG. 9 illustrates a flow chart 80 of an exemplary method for using the thermic infusion system 10. In a step 82, the power source 46 and the infusion fluid 16 may be connected to the thermic infusion system 10. In a step 84, the infusion fluid 16 may flow through the tubal body 18 of the thermic infusion system 10. In a step 86, one or more sensors 48 may obtain sensing information (e.g., temperature) related to the infusion fluid 16 and provide the sensing information to the control unit 44. In a step 88, the control unit 44 may analyze the sensing information and determine the amount of energy (e.g., electrical energy) to provide to the tubal segments 24a and 24b, and more particularly, to the thermal elements 30 of the tubal segments 24a and 24b. Each tubal segment 24a and 24b may receive different amounts of energy (e.g., electrical energy). For example, the tubal segment 24a may receive a greater amount of electrical energy to provide more heat to the infusion fluid 16 as compared to the amount of electrical energy provided to the tubal segment 24b as may the converse be true in an alternate embodiment. In a step 90, the thermal elements 30 may receive electrical energy and increase, decrease and/or stabilize the temperature of the infusion fluid 16. It should be noted that the control unit 44 may also signal the delivery of electrical energy to the tubal segments 24a and 24b prior to flow of the infusion fluid 16 through the tubal body 18, such that thermal regulation of the infusion fluid 16 may occur immediately upon flow of the infusion fluid 16 through the tubal body 18.

In some embodiments, the thermic infusion system 10 may be included within a kit. The kit may include one or more thermic infusions systems 10 and one or more power sources 46. Additionally, in some embodiments, the kit may include one or more bags of infusion fluid 16. To aid in use, the kit may include a quick start guide, a jump drive having video and/or text instruction, a written evaluation tool, and/or the like. The kit may be housed in a protective housing, for example.

As mentioned in the foregoing paragraphs, conventional (non-thermic) infusion tubes can be subjected to folding, crushing, and kinking, which can impede or even stop the flow of infusion fluids. Also, as previously mentioned, it was desired by the present inventor(s) to provide the thermic tubal segment with similar feel and/or handling characteristics of conventional intravenous (IV) tubing known within the art. The present inventors realized that, in some embodiments, the thermic infusion system's tubal segment should be resistant to kinking, such as when coiled for packaging, and/or when uncoiled during handling and use. If a kink in the tubal segment occurs, the tubal segment preferably is designed in a manner which allows it to autonomously rebound from such kink, fold or crush, thereby reopening the internal channel for flow of the infusion fluids without requiring manual manipulation to recover the shape and function of the tubal segment or tubal body.

One attempt to solve this problem in medical devices such as catheters and cannulas has employed an outer shell which is harder and more rigid than any other internal layers of the tubing. This approach yields such a rigid structure that it can be used to push, manipulate, and even puncture tissue. However, for an infusion set, such high structural rigidity is inappropriate because it poses a difficult handling problem for users, and may place unacceptably high lateral forces on an infusion needle during use.

Another attempt to solve this problem found specifically in the thermic infusion arts has been to use an embedded metal heating element as a structural reinforcement member to prevent or minimize folding, crushing, and kinking. This approach also creates a tube which may be too rigid for practical use as an infusion tube.

Both of these approaches lead away from the inventors' objective to provide a thermic infusion tube which has similar feel and handling characteristics as conventional IV tubing, which is soft enough to crush temporarily, but elastic enough to resist yielding or permanent shape distortion, and resilient enough to rebound into the desired shape and dimensions.

So, embodiments according to the present invention employ an opposite approach, in a manner of speaking, from those previously known in the relevant arts. First, the inventors decided to minimize the thickness of the embedded heating element, which reduces its structural contribution to the tube construction. Therefore, the present solution and various embodiments of it do not rely upon the mechanical strength of the heating element to either resist folds, bends and kinks, or to rebound after such. Second, the inventors have developed, through engineering calculations, simulations and experimentation, a structure in which the thinner inner sheath is structurally harder and more resilient than the thicker outer sheath, as will be described in more detail in the following paragraphs, rather than having the outer sheath more rigid than the inner sheath. Third, the inventors' solutions generally do not resist kinking, crushing or folding any more so than conventional IV tubing, unlike the other attempts in the art to prevent these from occurring. Rather, the present solution and various embodiments of it provide for autonomous rebound, fully expecting that folding, kinking, bending and crushing may occur under normal use.

Previously, in FIGS. 1-4, the tubal segment 24b, as also applied to the tubal segment 24a, was shown generally including an inner sheath 28, a thermal element 30, and an outer sheath 32. Referring now to FIG. 12A, in the one or more autonomous rebounding embodiments, a tubal segment normally assumes an un-deformed, essentially straight or slightly curved shape to allow for free flowing of the infusion fluid through the channel formed therein, essentially parallel or co-axial 123 to the tubal segment. However, as shown in FIG. 12B, when forces such as a force from a first side 120 of the tube towards a second side 121 of the tubal segment are great enough, a fold or kink may develop along a transverse axis 122 essentially perpendicular to the original flow direction 123 of the infusion fluid.

Figure 12C:
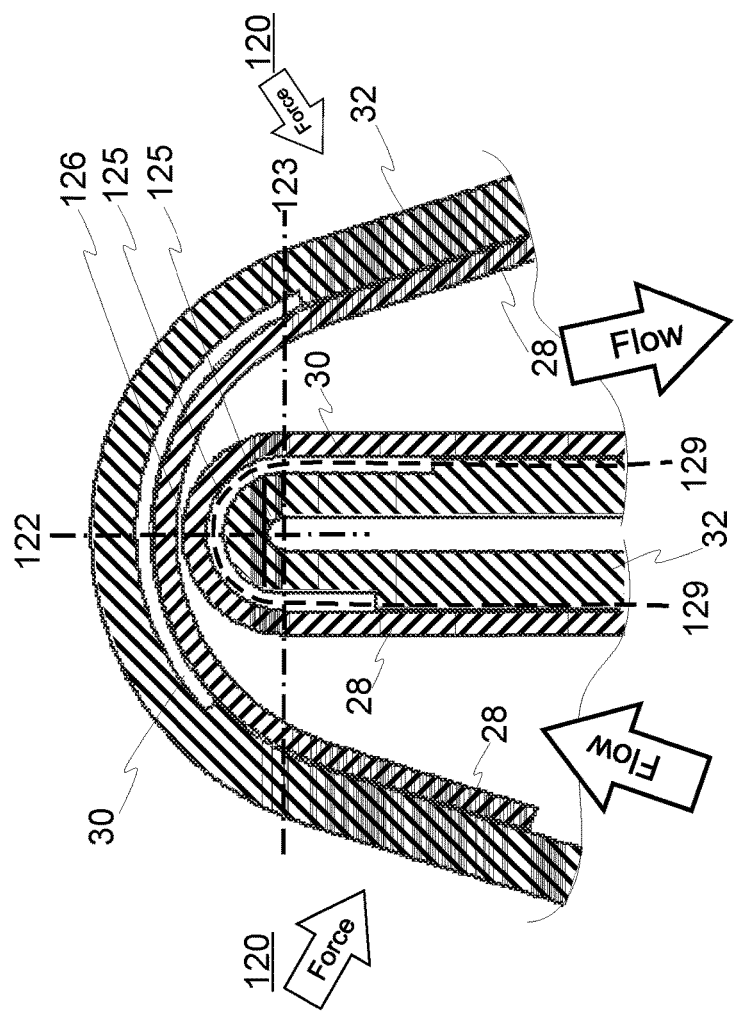
FIG. 12C provides a cross sectional side view of a portion of the tubal segment of FIG. 12b with a kink or bend formed in the tube segment.
Figure 12A:
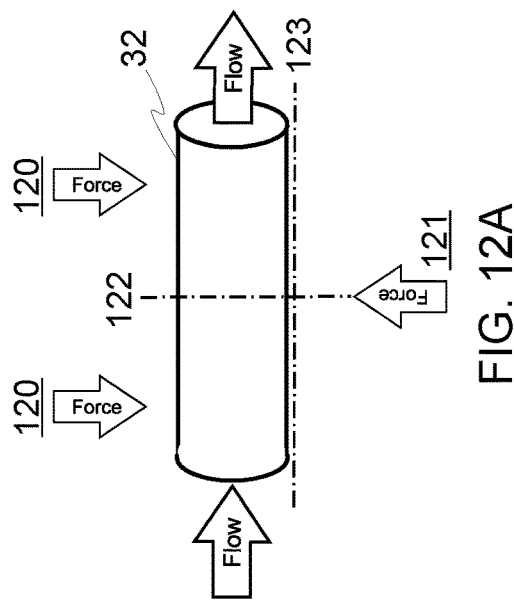
FIG. 12A illustrates a segment of tube in a normal shape prior to application of bending or folding force.
Figure 12B:
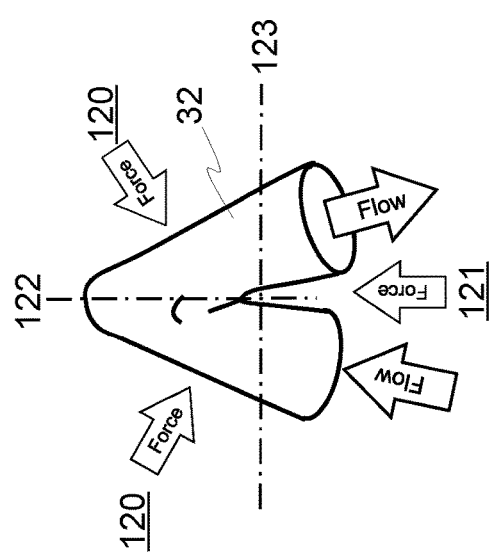
FIG. 12B illustrates the segment of tube as in FIG. 12A during or after a bending or kinking action has been exerted on the tube segment.

FIG. 12C illustrates a cross-sectional view of such a fold, in which the infusion fluid encounters a significantly narrowed passageway, and in which the infusion fluid may undergo a significant change in flow direction, both of which will contribute to flow resistance and obstruction.

To yield a solution which provides similar feel and handling characteristics to conventional IV tubing, the present inventors analytically evaluated and tested a variety of materials for the inner and outer sheaths, and a variety of construction embodiments using different materials for the sheaths and different thicknesses. When the thickness of the heater element 30 is minimized, and the tie layer is minimized, they provide little or no contribution to the overall resistance to crushing (rigidity) and likelihood to deform permanently (yielding) when bent, crushed, kinked or folded. The inventors considered tensile modulus of several material choices for the sheaths, which is a published by the suppliers of each material regarding its stretching characteristics. The inventors also wished to consider compressive modulus, which regards a material's characteristic to resist crushing, folding and kinking, but this is not a typically published criterion by the material suppliers. So, the present inventors utilized the published hardness factors for each of the considered materials, which is published, and can represent a localized characteristic to resist crushing, folding and kinking, as a proxy for compressive modulus. Other limitations to material selection and relative sheath thickness included opacity, for embodiments in which the flowing fluid was to be visible to the user, and ability to utilize the material in the manufacturing processes as described in the foregoing paragraphs.

Because there is metal in the wall of the tubal segment, a potential for the plastic to yield and for the metal to cause it to retain the deformed shape, instead of rebound or recover, existed. Minimizing the metal thickness reduced this potential. Then, the present inventors determined a number of combinations of inner and outer sheath materials and relative sheath thicknesses which would locate a neutral strain line towards the inside wall of the tube and further away from the outside of the wall of the tubal segment. By neutral strain line, we are referring to a line within the layers of materials where the material is neither stretched nor compressed when the tube is bent, folded, kinked or crushed. These combinations of materials and relative sheath thicknesses with a neutral strain line closer to the inside wall than to the outside wall provide larger bend radiuses for the metal-containing layer and the material interfaces. Further, by selecting a softer more pliable, less rigid material for the outer sheath than for the inner sheath, the neutral strain line also moves away from the midpoint of the combined tube wall thickness and towards the inside tube wall.

In FIG. 12C, one exemplary embodiment is shown which achieved a neutral strain line 129 which is closer, at the bend or crush, to the inside wall 126 of the tube than it is to the outside wall 125 of the tube at the minimum bend radius (intersection of axes 122 and 123).

Figure 13C:
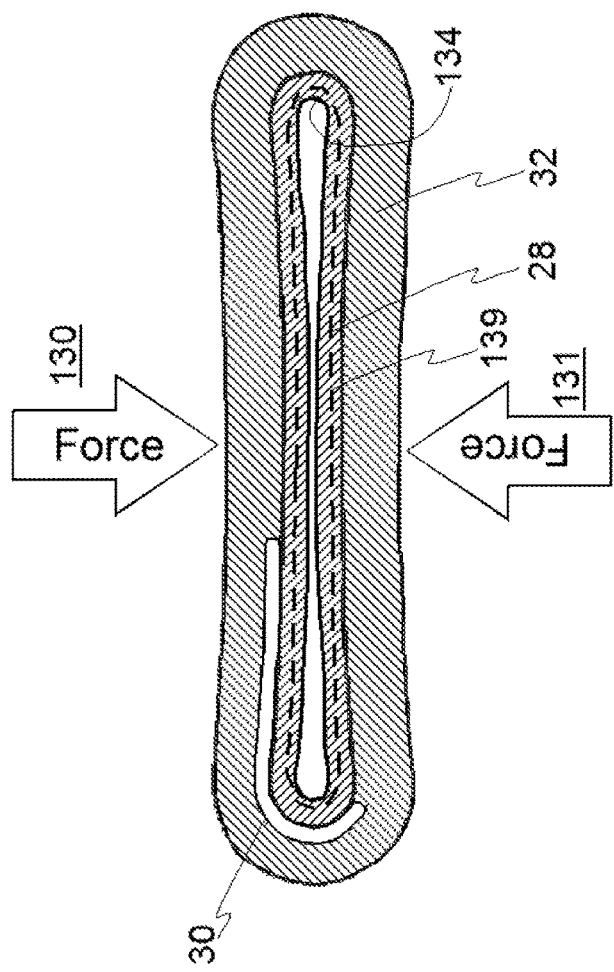
FIG. 13C provides a cross sectional axial view of a portion of the tubal segment with a crush or pinch formed in the tube segment.
Figure 13A:
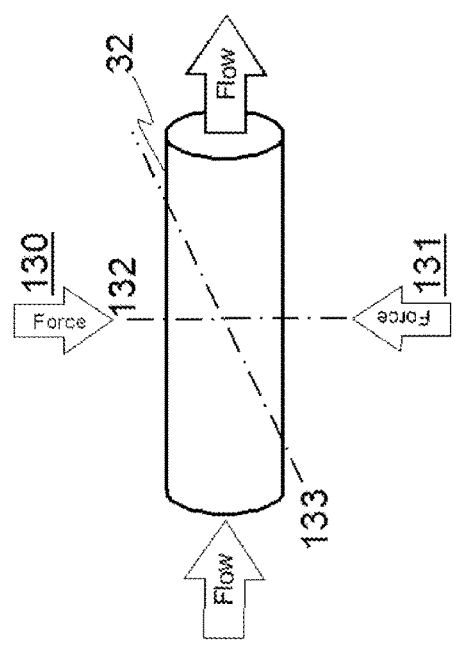
FIG. 13A illustrates a segment of tube in a normal shape prior to application of crushing or pinching force.
Figure 13B:
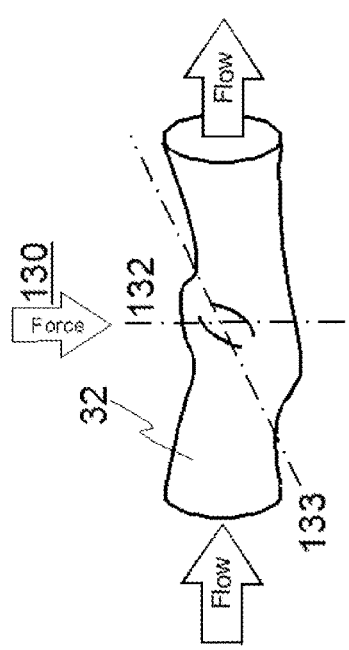
FIG. 13B illustrates the segment of tube as in FIG. 13A during or after a crushing or pinching action has been exerted on the tube segment.

Referring now to FIG. 13A, which is similar to FIG. 12A for reference, a tubal segment may also be crushed or pinched, as shown in FIG. 13B, by a force or forces 130 to 131 perpendicularly 132 through the tube segment's direction of fluid flow, which can cause a flattening (out of round) across the tubal segment 133. FIG. 3C shows an axial cross section view of such a pinched or crushed tubal segment, which also is somewhat representative of what could be an axial view relative to the fold, bend or kink of FIG. 12B. In this view of FIG. 13C, the intersection of axes 132 and 133 would appear near the inside radius 134, and the neutral strain line 139 is located closer to the inside wall of the inside sheath than it is to the outside wall of the outside sheath.

A tubal segment structure having a neutral strain line closer to the inside wall of the inside sheath than the outside wall of the outside sheath was achieved using the aforementioned dimensions of approximately 0.15 mm for the inner sheath 28 thickness, and approximately 0.39 mm for the outer sheath 32 thickness, when using BASF™ Elastollan 1154D or similar for the inner sheath and Teknor® Apex 3301-65 for the outer sheath. This outer-to-inner thickness ratio of 0.39 mm to 0.15 mm, or 2.6 (dimensionless), was found to be optimal in at least one embodiment. Other ratios ranging from a minimum of 1.3 to a maximum of 3.9 may produce similar acceptable and desirable feel and handling characteristics with the rebound and recovery performance as desired. Other materials suitable for the inner sheath include BASF™ Elastollan 1164D, Lubrizol™ Pellathane 2363-55D, and Pebax™ 633, and their equivalents, and other materials suitable for the outer sheath include non-DEPH PVC, Lubrizol™ TecoFlex EG-80A, Pebax™ 2533, Pebax™ 3533, and their equivalents, may produce similar acceptable and desirable feel and handling characteristics with the rebound and recovery performance as desired. The present inventors expect that other materials and other thicknesses may be suitable for achieving the desired neutral strain line position in alternative embodiments for the same or different infusion fluids.

As previously discussed, inserting the tubal segments into the control unit may automatically turn power on to the system in some embodiments. And, in other embodiments, a user control may be provided to turn on, and optionally off, the system.

The present patent application discloses an enhancement to many embodiments to automatically detect a dry infusion tube, and to take certain remedial actions, such as, but not limited to, a combination of alerting the user (e.g., turn on, off or flash an LED, issue a beep, rumble, etc.), preventing or removing power from the thermal heating elements of the dry tubal segment(s), and turning the control unit off. These remedial actions may be taken in combinations and sub-combinations, as well, such as issuing a visual user alert for an initial period of time (e.g., silent flashing LED), followed by issuing an audible user alert for a second period of time (e.g., a beep or rumble), followed by powering down the heating elements and/or the entire system. In some embodiments, the user may be provided an override control, such as a button or disconnect-reconnect time, to disable the automatic remedial actions.

For the purposes of the present disclosure, we can distinguish the difference between flow detection and dry tube detection by recognizing that flow, in and of itself, requires wet (fluid filled) tube. Even when a fluid flow rate is zero (stagnant, still), the tube itself is still filled with a thermal mass other than air, and the thermal units will have that fluid thermal mass (the infusion fluid) to which to transfer thermal energy. However, in a dry tube, there is no flow of course, and there is no fluid thermal mass to receive the thermal energy being dissipated from the thermal heating units, and thus the thermal energy can not only be wasting critical battery energy, but also potentially causing thermal damage to the structures of the system and/or nearby items such as packaging, clothing, etc.

In any or all of these enhanced embodiments, a scenario in which the infusion fluid has not filled the tubal segment(s) is comprehended and handled. Such scenarios may occur for many reasons, including but not limited to the user has not spiked an IV bag prior to plugging in the control unit to the tubal segments, the user has not released a roller clamp which is preventing infusion fluid flow from the bag into the tubing segment(s), there is another blockage, crimp or kink somewhere between the thermal tubing segment(s) and the infusion fluid source, and the infusion fluid source is empty, frozen, clumped, frozen, etc. Since certain infusion fluids such as saline solution are relatively invisible in a transparent IV set, and since these IV sets are often used in low-light and no-light conditions, a user may not be able visually verify that the infusion fluid has entered and filled the thermal tubing segment(s). Thus, an automatic dry tubing detection and remediation feature is a useful enhancement to the foregoing several embodiments of the present invention.

Optical detection of a dry tube is an option for embodiments in which only relatively opaque infusion fluids are to be handled by the system, but optical detection may not perform satisfactorily for embodiments in which relatively transparent infusion fluids are also expected to be transfused. The present inventors, therefore, have discovered a previously thought-to-be error in the negative thermal coefficient (NTC) thermistors can be utilized in a positive and beneficial manner.

Those skilled in the arts of using NTC and positive thermal coefficient (PTC) thermistors are aware of a phenomenon referred to as "self-heating" error. These thermistors present, at each temperature of the device, a certain amount of resistance, which causes a voltage drop across the device. Whereas current flows through the device during use as a temperature sensor, one can determine the power dissipated by the device using the voltage drop across it and the current flow through it in a convention manner using Ohm's law. The thermistor device generates a small amount of heat due to the current flowing through it while it is being used to detect a temperature of an ambient surrounding or thermally-connected mass, which causes a "self-heating" error factor to be injected into the sensing of temperature from the sensor device. While NTC devices are much less linear than PTC devices in their resistance-temperature response curves, both types of devices exhibit this error to some amount. Circuit designers typically seek to minimize self-heating error by providing greater thermal conductivity between the device and the mass to be measured, and by using the device with the minimum amount of current flow through the device for a minimum amount of time to obtain the necessary precision of temperature measurement for the system application in which the device is employed. For example, in the embodiment(s) described in the foregoing paragraphs, the control unit, when making normal temperature measurements of the infusion fluid, applies voltage to the thermistor for a very short period of time, such as a few microseconds. This allows a reading to be taken from the thermistor before it has heated appreciably due to self-heating, and thus the reading has minimal self-heating error.

The present inventors, however, have recognized that this conventionally-viewed detraction from thermistors can also be employed for a positive benefit to detect a dry tube. When an infusion tube is dry, the thermal mass surrounding the thermistor is minimal, reduced to simply the structure of the tubing segment itself, the ambient air or surface outside the tube, and the air in the tube. Thus, the present inventors discovered that it is predicable using the known response curves of a specific thermistor device how much temperature rise will be "sensed" by the thermistor due to unloaded (no fluid thermal mass) self-heating in any particular thermo-mechanical embodiment of the present invention when the tubal segment is dry when voltage is applied to the thermistor for a period of time, such as 2 seconds in some particular embodiments, than the voltage is applied to make a normal thermal measurement of a wet tube, such as a few microseconds. Other embodiments may use other greater or shorter time periods.

As shown in FIG. 11B, a thermistor such as a TDK™ brand NTCG163JF103F is employed in at least one embodiment. Its self-heating error contribution to its temperature sensing curves due to self-heating properties can be found in its data sheet denoted as "dissipation factors". Data sheets typically provide such information based on a presumption of operation in free air, for example, and are not directly applicable to specific design situations which do not match the presumption conditions. So, for embodiments of the present invention, thermal performance calculations using computer-aided design and experimental verification can be employed to determine dissipation factors of the specific thermistors when used in a specific thermo-mechanical system surrounded by attached printed circuit board(s), plastic tube connectors, layers of plastic in the tube, and the metal heating element within a volume surrounding the thermistor device.

In the one or more exemplary embodiments described in the foregoing paragraphs using the circuit boards, plastics, and dimensions set forth, it has been determined empirically and confirmed experimentally that a thermistor will self-heat 5 to 6 degrees Centigrade within 2 seconds of application of sensing voltage and current when the tube is dry (no fluid thermal mass), but will heat slower (less than 5 to 6 degrees) within 2 seconds of applying sensing voltage and current to the thermistor(s) when the tube is filled with any of the anticipated infusion fluids of the exemplary designs (e.g., blood, blood components, and saline solution). Other embodiments may use other greater or shorter periods of time, other greater or lesser thresholds for temperature rise, or a combination of other period of time and other temperature thresholds.

Figure 14:
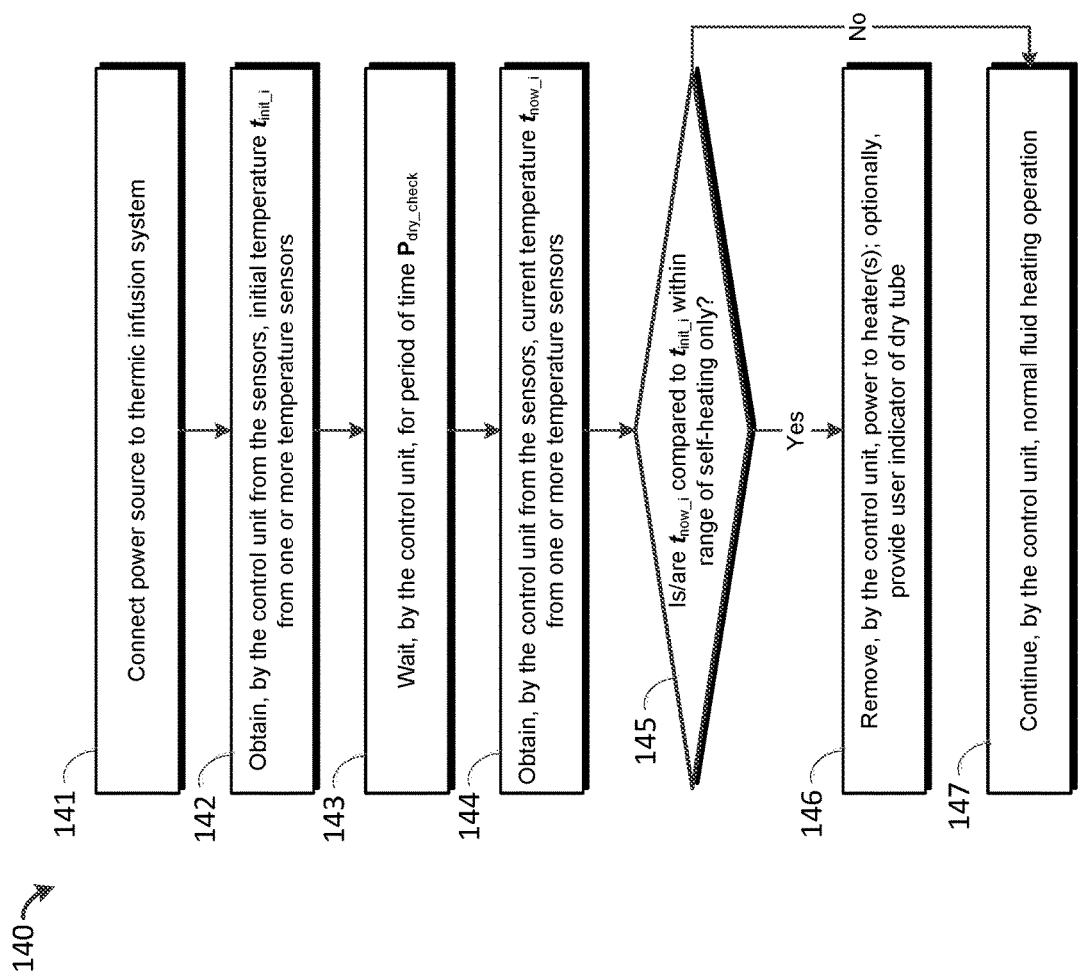
FIG. 14 illustrates a logical process according to at least one embodiment of the present invention for detecting a dry segment of infusion tube.

Turning to FIG. 14, an exemplary logical process 140 to be incorporated into one or more enhanced embodiments according to the invention is shown. When a power source is connected or engaged 141 to the thermic infusion system, the control unit will obtain 142 an initial temperature value $t_{init\_i}$ from one or more of i thermal sensors, such as NTC thermistor(s) by applying a voltage to the one or more thermistors, for example. Then, the control unit may wait 143 a specified period of time, while continuing to apply the voltage to the thermal sensor(s), such as 2 seconds in at least one exemplary embodiment, to obtain 144 subsequent temperature values $t_{now\_i}$ from the corresponding one or more of i thermal sensors.

If a comparison 145 of the initial and current temperature value(s) of the extended voltage-application period reveals temperature increase(s) which are primarily due to thermistor self-heating, such as ~5-6 degrees Centigrade in some embodiments, in consideration of specific thermistor non-linearity and static thermal masses of the system structure are factored, then one or more remedial action(s) are automatically performed 146, such as automatically preventing, by the control unit, power being applied to the heating elements, issuing user alerts, etc. In some embodiments, the regulating controls may be modified according to the detection of a dry tube in other ways, such as reducing the thermal element energy to a non-zero value.

In this manner, the self-heating error phenomenon, which is generally considered undesirable according to conventional wisdom is utilized, in conjunction with pre-determined structural thermal load characteristics of the specific embodiments of the present invention, to detect and respond, automatically, to dry tube conditions.

It should be noted that the thermic infusion system 10 may be used and/or included within other systems known within the art. For example, the thermic infusion system 10 may be used in heating for a dialysis system, chemotherapy system, blood exchange system, and/or the like. Further, one or more elements of the thermic infusion system 10 may be included within other systems known within the art.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and claimed herein.

CONCLUSION

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof, unless specifically stated otherwise.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

It will be readily recognized by those skilled in the art that the foregoing example embodiments do not define the extent or scope of the present invention, but instead are provided as illustrations of how to make and use at least one embodiment of the invention. The following claims define the extent and scope of at least one invention disclosed herein.

What is claimed is:

1. A thermic infusion system, comprising:
    a thermal tubing system comprising:
        at least one tubal segment having a hollow cylindrical body for conveying an infusion fluid therethrough;
        at least one thermal element configured to heat the hollow cylindrical body of the at least one tubal segment;
    an electronic control unit; and
    at least one thermistor sensor positioned within the thermal tubing system and configured to provide temperature sensing information from within the hollow cylindrical body to the electronic control unit, wherein the at least one thermistor sensor exhibits a predictable self-heating error;
    wherein the electronic control unit is electronically connected to the at least one thermistor sensor and configured to:
        apply voltage and current to the at least one thermistor sensor for a first period of time sufficiently long enough to produce and to sense the predictable self-heating error when the at least one tubal segment contains no fluid thermal mass,
        apply voltage and current to the at least one thermistor sensor for a second period of time sufficiently short enough to sense a temperature within the hollow cylindrical body of the at least one tubal segment without producing the predictable self-heating error when the at least one tubal segment contains a fluid thermal mass,
        determine, according to the sensed self-heating error and the sensed temperature within the hollow cylindrical body, that the hollow cylindrical body is dry, and
        responsive to the determination that the hollow cylindrical body is dry, regulate an amount of energy provided to the at least one thermal element to implement at least one remedial action.

2. The thermic infusion system as set forth in claim 1 wherein the first period is 2 seconds.

3. The thermic infusion system as set forth in claim 1 wherein the at least one thermistor sensor comprises a Negative Temperature Coefficient (NTC) thermistor.

4. The thermic infusion system as set forth in claim 1 wherein the first period is 2 seconds, wherein the at least one thermistor sensor comprises a Negative Temperature Coefficient (NTC) thermistor, and wherein the applying voltage and current to the at least one thermistor sensor for the first period of time comprises detecting a self-heating rise of at least 5 degrees Centigrade of the at least one thermistor sensor.

5. The thermic infusion system as set forth in claim 1 wherein the fluid thermal mass comprises one or more fluids selected from the group consisting of whole blood, plasma, and saline solution.

6. The thermic infusion system as set forth in claim 1 wherein the at least one remedial action comprises issuing at least one user alert.

7. The thermic infusion system as set forth in claim 6 wherein the at least one user alert comprises at least one user alert selected from the group consisting of illuminating an indicator, extinguishing an indicator, flashing an indicator, issuing an audible tone, and issuing a tactile feedback rumble.

8. The thermic infusion system as set forth in claim 1 wherein the regulating of the amount of energy provided to the at least one thermal element comprises one or more regulating controls selected from the group consisting of preventing energizing the at least one thermal element, and reducing energizing of the at least one thermal element to a non-zero level.

9. A method of controlling a thermic infusion system comprising:
    applying voltage and current, by an electronic control unit, to at least one thermistor sensor configured to provide temperature sensing information from within a hollow cylindrical body of at least one tubal segment of a thermal tubing system for a first period of time sufficiently long enough to sense a predicatable self-heating error of the at least one thermistor sensor when the at least one tubal segment contains no fluid thermal mass;
    applying voltage and current, by the electronic control unit, to the at least one thermistor sensor for a second period of time sufficiently short enough to sense a temperature within the hollow cylindrical body of the at least one tubal segment without producing the predictable self-heating error when the at least one tubal segment contains a fluid thermal mass;

determining, by the electronic control unit, according to the sensed self-heating error and the sensed temperature within the hollow cylindrical body, that the hollow cylindrical body is dry; and responsive to determining the hollow cylindrical body is dry, regulating, by the electronic control unit, an amount of energy provided to the at least one thermal element to implement at least one remedial action.

10. The method as set forth in claim 9 wherein the first period is 2 seconds.

11. The method as set forth in claim 9 wherein the at least one thermistor sensor comprises a Negative Temperature Coefficient (NTC) thermistor.

12. The method as set forth in claim 9 wherein the first period is 2 seconds, wherein the at least one thermistor sensor comprises a Negative Temperature Coefficient (NTC) thermistor, and wherein the determining of a dry hollow cylindrical body comprises detecting a self-heating rise of at least 5 degrees Centigrade of the at least one thermistor sensor.

13. The method as set forth in claim 9 wherein the fluid thermal mass comprises one or more fluids selected from the group consisting of whole blood, plasma, and saline solution, and wherein the determining is performed according to one or more pre-determined structural thermal load characteristics of the at least one tubal segment.

14. The method as set forth in claim 9 wherein the at least one remedial action comprises issuing, by the electronic control unit, at least one user alert.

15. The method as set forth in claim 14 wherein the at least one user alert comprises at least one user alert selected from the group consisting of illuminating an indicator, extinguishing an indicator, flashing an indicator, issuing an audible tone, and issuing a tactile feedback rumble.

16. The method as set forth in claim 9 wherein the regulating of the amount of energy provided to the at least one thermal element comprises at least one regulating control selected from the group consisting of preventing energizing the at least one thermal element, and reducing the amount of energy provided to the at least one thermal element to a non-zero level.

\* \* \* \* \*